(12) United States Patent
Fujii et al.

(10) Patent No.: US 11,083,489 B2
(45) Date of Patent: Aug. 10, 2021

(54) TROCAR WITH DEPLOYABLE CAMERA

(71) Applicant: KYOCERA CORPORATION, Kyoto (JP)

(72) Inventors: Takaharu Fujii, Tokyo (JP); Takashi Saotome, Tokyo (JP); Hiroki Taoka, Sendai (JP)

(73) Assignee: KYOCERA Corporation, Kyoto (JP)

( * ) Notice: Subject to any disclaimer, the term of this patent is extended or adjusted under 35 U.S.C. 154(b) by 478 days.

(21) Appl. No.: 16/000,985

(22) Filed: Jun. 6, 2018

(65) Prior Publication Data

US 2018/0289391 A1 Oct. 11, 2018

Related U.S. Application Data

(63) Continuation of application No. PCT/JP2016/086453, filed on Dec. 7, 2016.

(30) Foreign Application Priority Data

Dec. 7, 2015 (JP) .............................. JP2015-238969
Feb. 12, 2016 (JP) .............................. JP2016-024898

(51) Int. Cl.
*A61B 17/34* (2006.01)
*A61B 1/313* (2006.01)
*A61B 1/05* (2006.01)
*A61B 90/00* (2016.01)
*A61B 1/00* (2006.01)

(52) U.S. Cl.
CPC ........ *A61B 17/3415* (2013.01); *A61B 1/0008* (2013.01); *A61B 1/00154* (2013.01); *A61B 1/00179* (2013.01); *A61B 1/00183* (2013.01); *A61B 1/05* (2013.01); *A61B 1/313* (2013.01); *A61B 17/3417* (2013.01); *A61B 17/3462* (2013.01); *A61B 17/3494* (2013.01); *A61B 90/361* (2016.02); *A61B 2017/3454* (2013.01); *A61B 2090/371* (2016.02)

(58) Field of Classification Search
None
See application file for complete search history.

(56) References Cited

U.S. PATENT DOCUMENTS

2002/0049367 A1* 4/2002 Irion ...................... A61B 17/29
                                                                600/173
2006/0135972 A1   6/2006 Zeiner
(Continued)

FOREIGN PATENT DOCUMENTS

JP        05115425 A   *  5/1993  ......... A61B 1/00193
JP     2004167094 A       6/2004
(Continued)

*Primary Examiner* — John P Leubecker
(74) *Attorney, Agent, or Firm* — Viering, Jentschura & Partner MBB

(57) ABSTRACT

A trocar for inserting a surgical instrument in a body may include: a pipe including an outer cylinder relatively slidable in an axial direction, and an inner cylinder; a head located on a proximal end of the pipe; a camera that is journaled in a distal end notch of the pipe inner cylinder so as to be turnable between a deployment state in which the camera rotates to the outside of the pipe and a storage state in which the camera is stored inside the pipe; and a coil spring biasing the camera to the deployment state.

20 Claims, 22 Drawing Sheets

(56) References Cited

U.S. PATENT DOCUMENTS

| | | | |
|---|---|---|---|
| 2007/0073109 A1* | 3/2007 | Irion | A61B 1/0684 600/179 |
| 2008/0033450 A1* | 2/2008 | Bayer | A61B 17/3417 606/108 |
| 2009/0299363 A1* | 12/2009 | Saadat | A61B 5/6882 606/41 |
| 2010/0076478 A1 | 3/2010 | Smith | |
| 2010/0081875 A1* | 4/2010 | Fowler | A61B 1/00188 600/114 |
| 2011/0160535 A1* | 6/2011 | Bayer | A61B 1/05 600/109 |
| 2011/0306832 A1* | 12/2011 | Bassan | A61B 1/00096 600/109 |
| 2013/0046137 A1* | 2/2013 | Zhao | A61B 1/00181 600/102 |
| 2013/0282041 A1* | 10/2013 | Gunday | A61B 17/3421 606/170 |
| 2014/0107417 A1* | 4/2014 | McKinley | A61B 90/30 600/112 |
| 2014/0180001 A1* | 6/2014 | von Grunberg | A61B 1/00064 600/104 |
| 2014/0194683 A1 | 7/2014 | Nakaguchi | |
| 2014/0221748 A1* | 8/2014 | Kikuchi | A61B 1/00006 600/111 |
| 2014/0228644 A1* | 8/2014 | Ikenaga | A61B 1/00193 600/166 |
| 2014/0320621 A1* | 10/2014 | Sonnenschein | H04N 5/2254 348/76 |
| 2015/0289755 A1* | 10/2015 | Voros | A61B 1/3132 600/109 |
| 2016/0073855 A1* | 3/2016 | Farr | A61B 1/00154 600/109 |
| 2016/0220313 A1* | 8/2016 | Durvasula | A61B 1/00009 |
| 2016/0377947 A1* | 12/2016 | Scepanovic | G02F 1/157 455/566 |

FOREIGN PATENT DOCUMENTS

| | | |
|---|---|---|
| JP | 2006167475 A | 6/2006 |
| JP | 2013046789 A | 3/2013 |
| JP | 2014132979 A | 7/2014 |
| JP | 2016016053 A | 2/2016 |
| JP | 2016150216 A | 8/2016 |
| WO | 2009144729 A1 | 12/2009 |

* cited by examiner

Example 1

Example 2

Example 3

Example 4

Example 5

Example 6

Example 7

Example 1

Example 2

Example 3

Example 4

Example 5

Example 6

Example 7

TROCAR WITH DEPLOYABLE CAMERA

RELATED APPLICATIONS

This application is a Continuation of PCT International Application No. PCT/JP2016/086453 filed on 7 Dec. 2016, which claims priority under 35 U.S.C § 119(a) to Japanese Patent Application No. 2015-238969 filed on 7 Dec. 2015 and Japanese Patent Application No. 2016-24898 filed on 12 Feb. 2016. All of which are hereby expressly incorporated by reference, in their entirety and for all purposes, into the present application.

TECHNICAL FIELD

The present disclosure relates to a trocar to be used in an endoscopic surgical operation.

BACKGROUND ART

In recent years, minimally invasive surgical operations, such as laparoscopic surgery, in which an endoscope is inserted in an abdominal cavity, are required in order to maintain and improve quality of life (QOL) of patients. In the laparoscopic surgery, carbon dioxide gas is injected into the abdominal cavity to inflate an abdominal wall, and a space and a visual field for a procedure are secured. Then, a small hole is made in the abdominal wall, an instrument called a trocar is inserted, a surgical instrument such as an endoscope (CCD camera) and a forceps is inserted in a body of the patient through the surgical instrument, and an operation is typically performed while an operator observes an image displayed on a monitor by the endoscope (see Patent Documents 1 and 2).

Since the number of inserted endoscopes is usually one in such a conventional endoscopic surgical operation, the visual field is limited and there is little information that an operator can make a determination by watching the monitor during the procedure. On the other hand, although the wider visual field can be secured by further inserting an additional endoscope, it is necessary to make a new hole in the body wall to insert the endoscope. This increases a burden on the patient. Therefore, there is a proposal that intends to expand an observation visual field in the laparoscopic surgery by attaching a small camera to the trocar to be used in the laparoscopic surgery (see Patent Document 3).

That is, Patent Document 3 adopts a mechanism in which the camera is stored inside the trocar when the trocar is inserted in the abdominal cavity, and the camera is deployed to the outside of the trocar at the time when a distal end of the trocar is inserted in the abdominal cavity.

However, since it is necessary to install, in the trocar, a mechanism that operates the storage and deployment of the camera, an inner diameter and an outer shape of the trocar are enlarged. This increases the burden on the patient.

Additionally, it is necessary to provide a plurality of lenses and a surface protection cover to the camera of the trocar, and it is necessary for the camera attached to the trocar to have a waterproof structure. Therefore, it is not easy to achieve reduction in the height (the thickness) of the camera.

PRIOR ART DOCUMENTS

Patent Documents

Patent Document 1: Japanese Unexamined Patent Publication No. 2013-046789
Patent Document 2: Japanese Unexamined Patent Publication No. 2006-167475
Patent Document 3: Japanese Unexamined Patent Publication No. 2014-132979

SUMMARY OF THE INVENTION

A trocar of the present disclosure, for inserting a surgical instrument in a body, comprises: a pipe including an outer cylinder relatively slidable in an axial direction, and an inner cylinder; a head located on a proximal end of the pipe, a camera that is journaled at a distal end notch of the inner cylinder so as to be turnable between a deployment state in which the camera turns to the outside of the pipe and a storage state in which the camera is stored inside the pipe; and a deployment and storage mechanism including an elastic member, in the inner cylinder, biasing the camera to the deployment state, and the slidable outer cylinder being configured to store the camera in the pipe against biasing force of the elastic member while sliding toward a distal end of the pipe.

Other trocar of the present disclosure, for inserting a surgical instrument in a body, comprises: a pipe including an outer cylinder relatively slidable in an axial direction, and an inner cylinder; a camera that is journaled at a distal end of the inner cylinder so as to be turnable between a deployment state in which the camera turns to the outside of the pipe and a storage state in which the camera is stored inside the pipe; and a deployment and storage mechanism including an elastic member, in the inner cylinder, biasing the camera to the deployment state, and the slidable outer cylinder being configured to store the camera in the pipe against biasing force of the elastic member while sliding toward a distal end of the pipe.

A trocar of the present disclosure, for inserting a surgical instrument in a body, comprises: a pipe having a camera disposed in a distal end; a head located on a proximal end of the pipe; and a connector provided on an outer surface of the head, and a cable for controlling the camera being connected to the connector. The connector is disposed at a position different from a mounting position of the camera in a circumferential direction of the head.

EMBODIMENTS FOR CARRYING OUT THE INVENTION

Hereinafter, an embodiment of the present disclosure will be described in detail with reference to the drawings.

<Overall Structure of Trocar>

Figure 1:
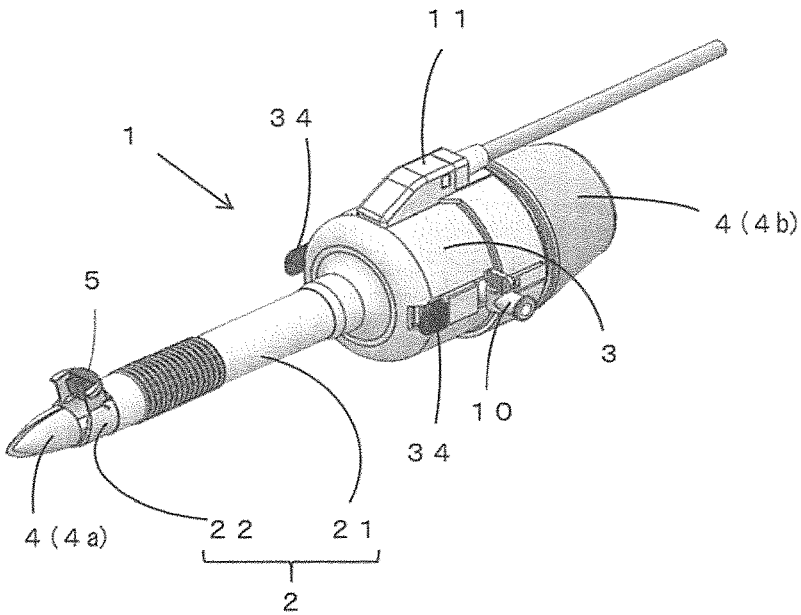
FIG. 1 is a perspective view illustrating a trocar in a camera deployment state according to an embodiment of the present disclosure.

FIG. 1 illustrates a trocar 1 according to an embodiment of the present disclosure. For example, the trocar 1 is used in the laparoscopic surgery. The trocar 1 includes a pipe 2 located on a distal end side (hereinafter, occasionally referred to as a "remote position") when viewed in a direction in which the trocar is inserted during surgery and a head 3 located on an proximal side (hereinafter, occasionally referred to as a "near side").

A trocar shaft 4 penetrating the pipe 2 from the head 3 is mounted on the trocar 1. A puncture portion 4a that punctures an abdominal cavity through a body wall is formed at a distal end of the trocar shaft 4, and a handle portion 4b is formed at a rear end of the trocar shaft 4. The puncture portion 4a has a conical shape such that the distal end of the puncture portion 4a agrees substantially with an inner diameter of the pipe 2. The handle portion 4b is used by an operator to perform an operation of inserting and extracting the trocar shaft 4 in and from the trocar 1.

Figure 2A:
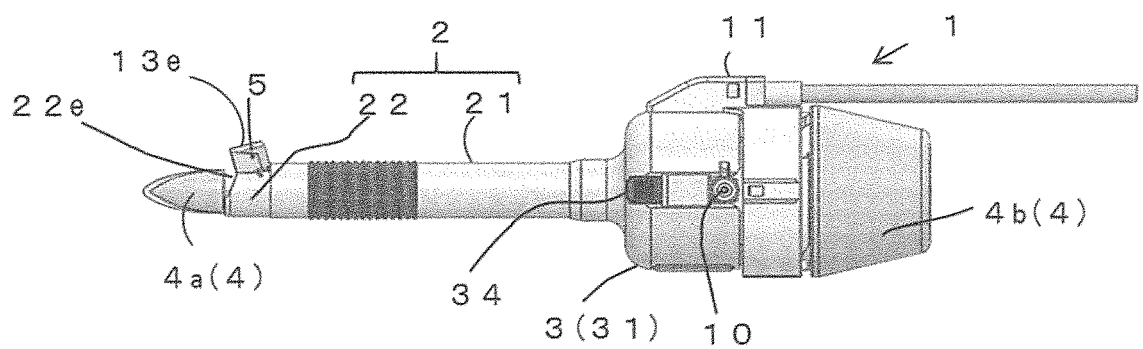
FIG. 2A is a side view illustrating the trocar in FIG. 1.
Figure 2B:
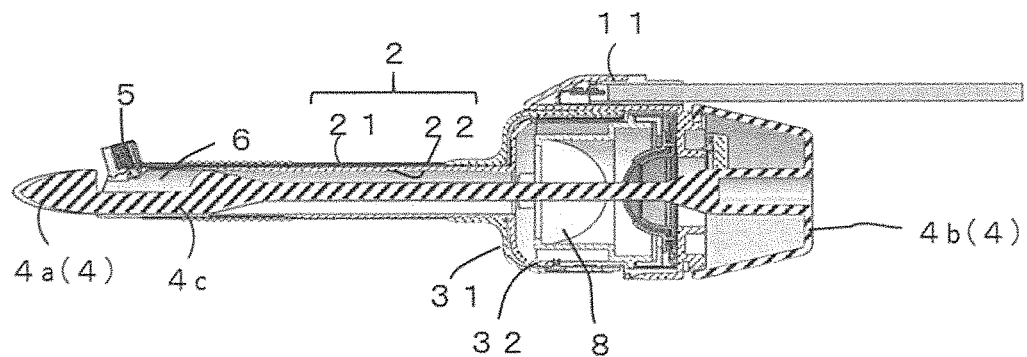
FIG. 2B is a sectional view illustrating the trocar in FIG. 1.
Figure 3A:
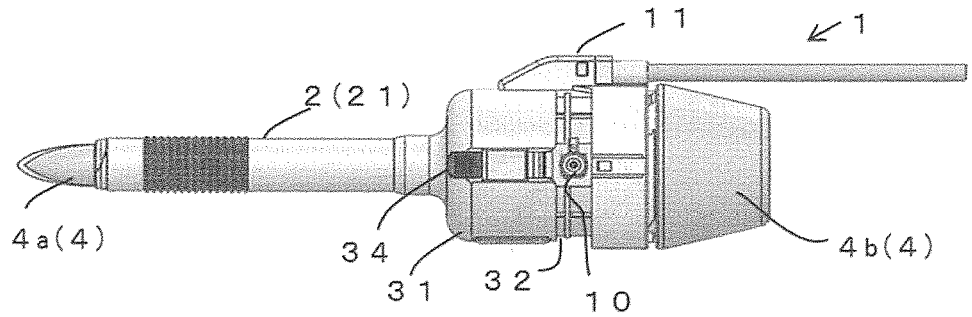
FIG. 3A is a side view illustrating the trocar in FIG. 1 in a camera storage state.
Figure 3B:
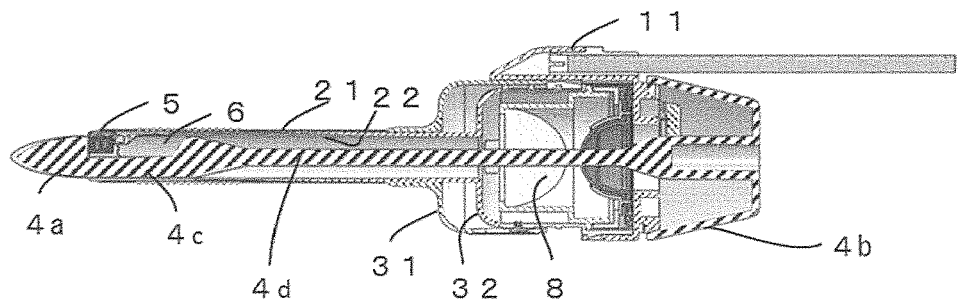
FIG. 3B is a sectional view illustrating the trocar in FIG. 1 in the camera storage state.

As illustrated in FIGS. 1, 2A, and 2B, the trocar 1 has a camera 5 as imaging means, the camera 5 being attached to the distal end of the pipe 2. FIGS. 1, 2A, and 2B illustrate a state in which the camera 5 is deployed. On the other hand, FIGS. 3A and 3B illustrate a state in which the camera 5 is stored in the pipe 2. As illustrated in FIG. 3B, a distal end portion 4c continuing to the puncture portion 4a of the trocar shaft 4 is formed in a columnar shape having an outer diameter substantially identical to the inner diameter of the pipe 2. In the storage state of the camera 5, a notch 6 is formed in a part of the distal end portion 4c in order to secure a storage space of the camera 5. A coupling portion 4d extending from the distal end portion 4c to the handle portion 4b has an outer diameter smaller than that of the distal end portion 4c. The reason why such a structure is adopted is that sufficient strength is ensured against large force applied in inserting the trocar 1 by supporting the distal end of the pipe 2 including the camera 5 from the inside of the pipe 2 using the distal end portion 4c having the large outer diameter.

When the pipe 2 has the inner diameter of 12.7 mm, the columnar distal end portion 4c preferably has the outer diameter of about 12.6 mm.

Figure 4A:
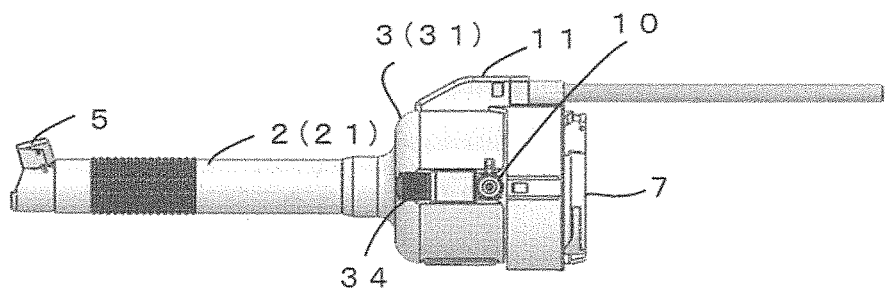
FIG. 4A is a side view illustrating the trocar with a trocar shaft removed from the trocar in FIG. 2A.
Figure 4B:
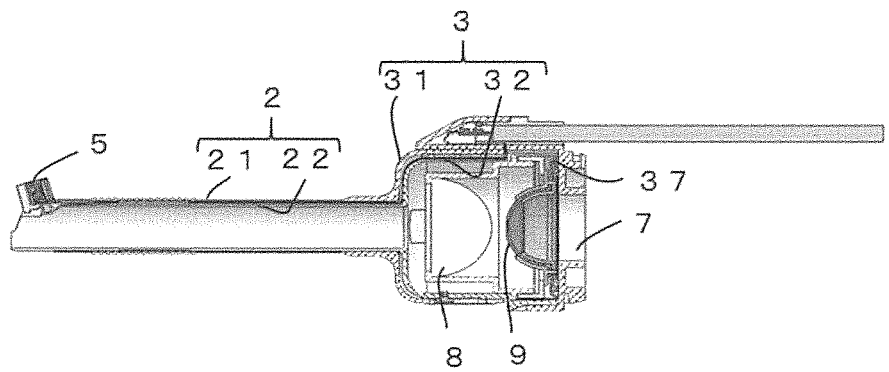
FIG. 4B is a sectional view illustrating the trocar with the trocar shaft removed from the trocar in FIG. 2B.

FIGS. 4A and 4B illustrate the trocar 1 in which the trocar shaft 4 is pulled out from the state in FIGS. 2A and 2B. As illustrated in FIG. 4B, the pipe 2 of the trocar 1 has a double structure including a outer cylinder 21 and a inner cylinder 22. The head 3 includes a head outer cylinder 31 integrally formed with the outer cylinder 21 and a head inner cylinder 32 integrally formed with the inner cylinder 22.

The outer cylinder 21 and the head outer cylinder 31 or the inner cylinder 22 and the head inner cylinder 32 may be integrally coupled or connected to each other.

<Head>

A structure of the head will be described below. The head inner cylinder 32 includes an air pipe 10 though which gas such as carbon dioxide gas and air is fed into the abdominal cavity (see FIG. 1). The gas fed from the air pipe 10 attached to the head inner cylinder 32 is fed into the abdominal cavity through the inner cylinder 22, and the inside of the abdominal cavity is pressurized.

Figure 5:
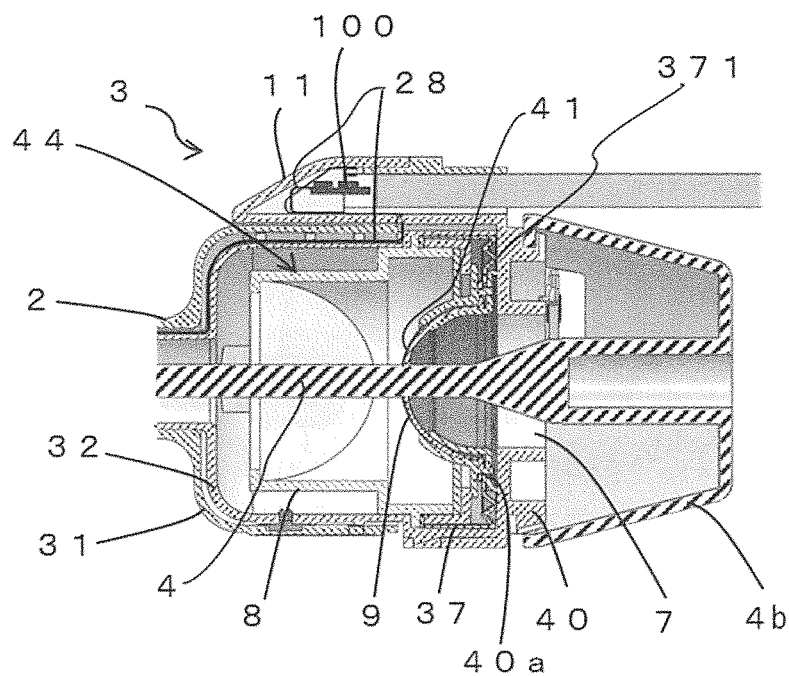
FIG. 5 is a sectional view illustrating a head of the trocar.
Figure 6:
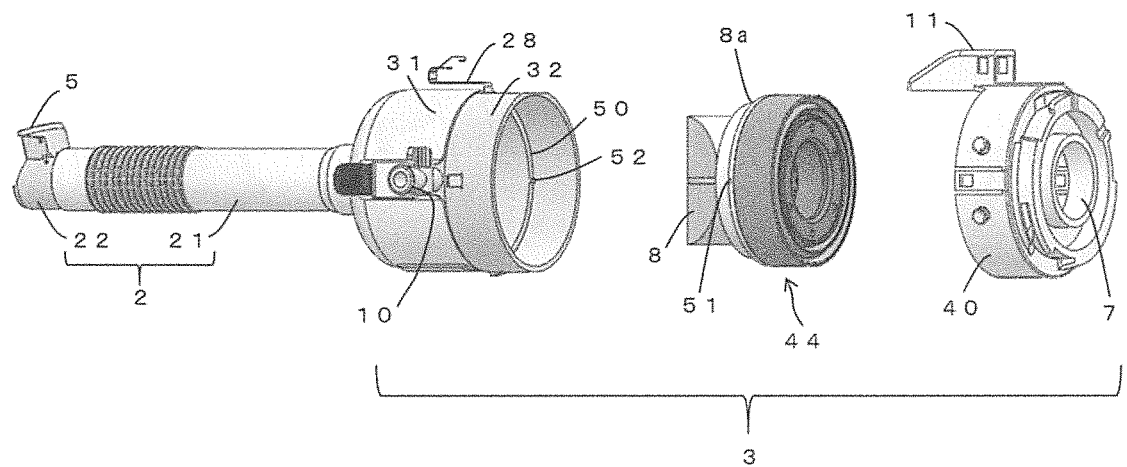
FIG. 6 is an exploded perspective view illustrating the trocar of the embodiment of the present disclosure.

As illustrated in FIGS. 5 and 6, the head 3 has the double structure including the head outer cylinder 31 and the head inner cylinder 32. An airtight structure unit 44 is accommodated in the head inner cylinder 32, and a plug member 40 is provided on a base end side of the head inner cylinder 32 in order to fix the airtight structure unit 44 to a predetermined position in the head inner cylinder 32. The head outer cylinder 31 and the head inner cylinder 32 in which the airtight structure unit 44 is accommodated constitute a head main body.

The plug member 40 includes, in its center portion, an opening 7 through which the trocar shaft 4 is inserted. In FIG. 5, the trocar shaft 4 is inserted in the opening 7, and the handle portion 4b is engaged with the plug member 40. After the trocar shaft 4 is pulled out, a surgical instrument such as a forceps (not illustrated, hereinafter occasionally referred to as a surgical instrument) can be inserted through the opening 7.

A connector 11 to which a flexible cable 28 (signal and power supply cable and FPC cable) extending from the camera 5 is connected is formed on an outer circumferential surface of the plug member 40.

The airtight structure unit 44 will be described below with reference to FIGS. 7 to 10.

Figure 7:
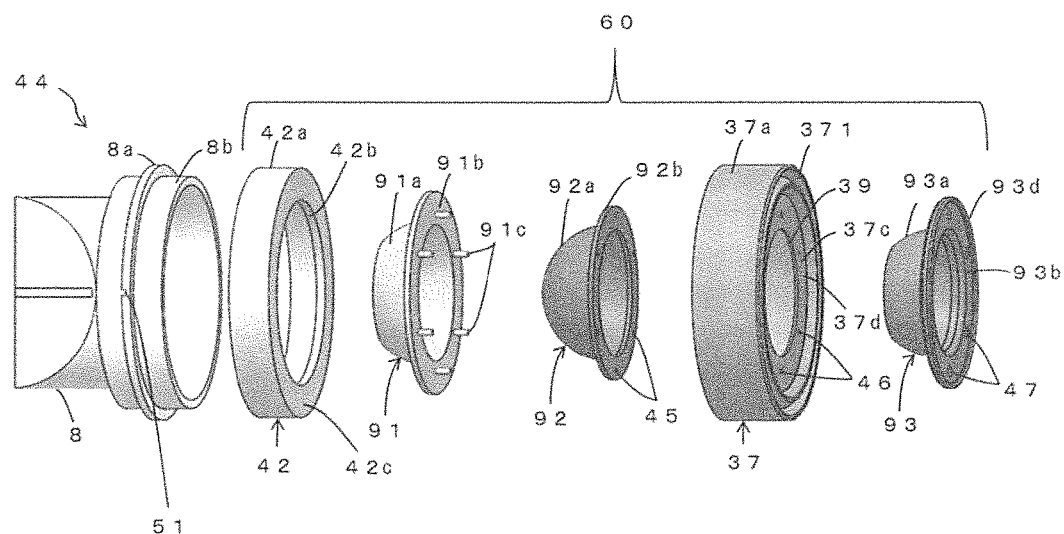
FIG. 7 is an exploded perspective view illustrating an airtight structure unit of the embodiment of the present disclosure.
Figure 8:
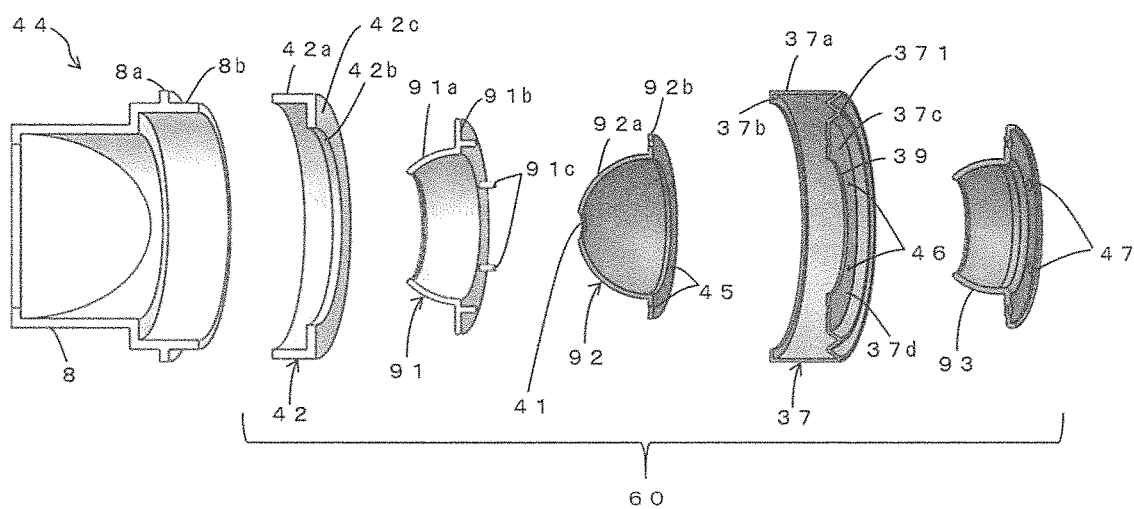
FIG. 8 is a broken exploded perspective view of FIG. 7.

As illustrated in FIGS. 7 and 8, the airtight structure unit 44 includes a duckbill valve 8 at the distal end side (remote position) of the head inner cylinder 32 and a seal unit 60 disposed from the duckbill valve 8 toward the near side (proximal side).

The duckbill valve 8 includes a flange 8a on an outer circumferential surface of the duckbill valve 8. On the other hand, a stepped portion 50 on which the flange 8a abuts is formed on an inner circumferential surface of the head inner cylinder 32 on which the airtight structure unit 44 is mounted (see FIG. 6). A recess 51 is formed on the distal end side of the flange 8a, while a protrusion 52 is formed in the stepped portion 50 so as to correspond to the recess 51. Consequently, the duckbill valve 8 can surely be positioned at a predetermined position in mounting the airtight structure unit 44 including the duckbill valve 8. Each of the recess 51 and the protrusion 52 may be provided, or pluralities of recesses 51 and protrusions 52 may be provided.

A seal unit 60 includes a seal holder 42, a dome type seal fixing distal end side mount 91, a dome type seal 92, an airtight rubber cover 37, and a dome type seal fixing near side mount 93 in order from the duckbill valve 8 toward the near side (proximal side). The seal unit 60 is a seal structure, which prevents leakage of the pressurized gas in the abdominal cavity by bringing the seal unit into close contact with a surgical instrument when the surgical instrument is inserted and used. The seal unit 60 is constructed with a plurality of members.

Figure 9:
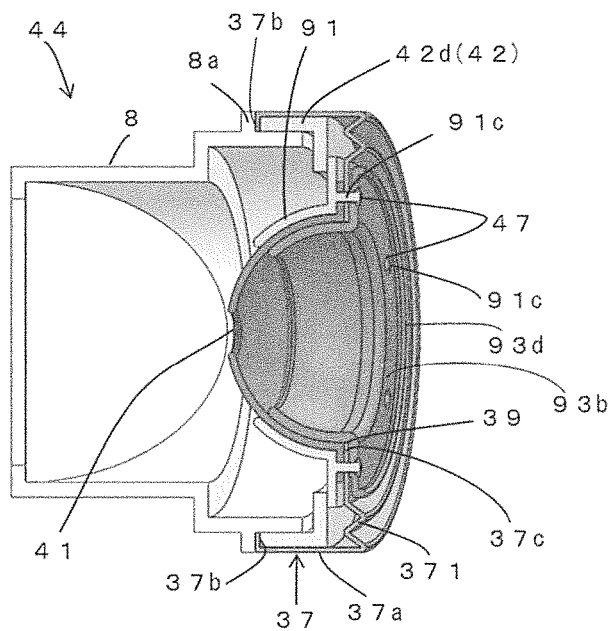
FIG. 9 is a broken perspective view illustrating an assembly state of the airtight structure unit.

The duckbill valve 8 is a duck beak-shaped valve mechanism, and partitions the opening 7 and the inside of the pipe 2. As illustrated in FIG. 9, the duckbill valve 8 is closed to prevent the leakage of the pressurized gas in the abdominal cavity before the trocar shaft 4 and a surgical instrument such as a forceps are inserted, and the trocar shaft 4 and the surgical instrument are inserted in the pipe 2 so as to push and open an openable port 81. The duckbill valve 8 is made of an elastomer material, such as silicone rubber, which is an elastic material.

Figure 10:
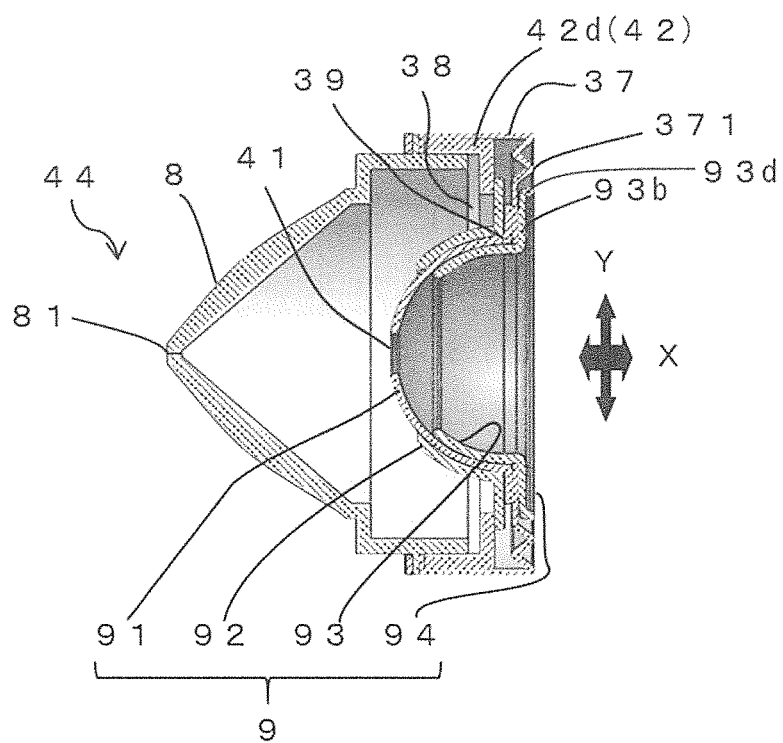
FIG. 10 is a sectional view illustrating a state in which the airtight structure unit in FIG. 9 is rotated by 90°.

FIG. 10 illustrates the airtight structure unit 44 rotated by 90 degrees from the state in FIG. 9.

Returning to FIGS. 7 and 8, the seal unit 60 will be described. The seal holder 42 is made of a resin material such as polycarbonate and acetal, and includes a large diameter portion 42a fitted in a cylindrical portion 8b on the near side of the flange 8a of the duckbill valve 8 and a flat portion 42c including a small diameter portion 42b that positions a flange 91b of the dome type seal fixing distal end side mount 91. The seal holder 42 functions as a holder that holds an airtight rubber cover (to be described later).

The dome type seal fixing distal end side mount 91 is made of a polycarbonate resin or the like, and constructed with a circumferential wall 91a in which the dome type seal 92 is fitted and the flange 91b. A plurality of pins 91c (six in FIG. 7) are integrally formed in the flange 91b.

The dome type seal 92 is made of an elastomer material, such as silicone rubber, which is an elastic material, and constructed with a seal main body 92a including an instrument insertion port 41 through which the trocar shaft 4 and other surgical instruments are inserted and a flange 92b. A positioning hole 45 through which the pin 91c provided on the dome type seal fixing distal end side mount 91 is inserted is made in the flange 92b.

The airtight rubber cover 37 is made of an elastomer material, such as silicone rubber, which is an elastic material, and has a function of coupling the duckbill valve 8 and the dome type seal 92 to enhance the airtightness therebetween. The airtight rubber cover 37 has a tubular portion 37a, a first small diameter portion 37b provided on the distal end side of the tubular portion 37a, and a second small diameter portion 37c provided on the near side. A bellows portion 371 is formed in the second small diameter portion 37c so as to be able to follow the movement of the dome type seal 92. A flat circumferential edge (flat portion) 37d is formed at a circumferential edge of the opening 39 on the inner diameter side of the bellows portion 371 provided in the second small diameter portion 37c, and a positioning hole 46 through which the pin 91c is inserted is made in the flat circumferential edge (flat portion) 37d.

The dome type seal fixing near side mount 93 is made of a resin material such as polycarbonate and polyacetal, and constructed with a circumferential wall 93a fitted in the dome type seal 92 and a flange 93b. A positioning hole 47 through which the pin 91c provided on the dome type seal fixing distal end side mount 91 is inserted is made in the flange 93b.

FIGS. 5, 9, and 10 illustrate the assembly state of the airtight structure unit 44. In the assembly, the flat portion 42c and the flanges 91b, 92b, 37d, and 93b of the four components, namely, the dome type seal fixing distal end side mount 91, the dome type seal 92, the airtight rubber cover 37, and the dome type seal fixing near side mount 93 are overlapped, and the pin 91c provided on the dome type seal fixing distal end side mount 91 is sequentially inserted in the holes 45, 46, 47 made in the airtight rubber cover 37 and the dome type seal fixing near side mount 93. Finally, after the distal end of the pin 91c is integrated by thermal caulking, the remote position side end edge 42d of the seal holder 42 is held by the first small diameter portion 37b provided on the distal end side of the airtight rubber cover 37, thereby assembling the seal unit 60.

A projection edge 93d extending toward the near side from the flat portion of the flange 93b is formed at the outer circumferential edge of the flange 93b of the dome type seal fixing near side mount 93 (see FIG. 7). As illustrated in FIG. 9, a projection amount of the projection edge 93d may be such that the pin 91c caulked by heat does not project from the projection edge 93d but is accommodated in the projection edge 93d.

By overlapping the flanges 91b, 92b, 37d, and 93b and integrating the dome type seal 92 in this way, the dome type seal 92 acts on the bellows portion 371 provided on the airtight rubber cover 37 in conjunction with the movement of the surgical instrument inserted in the instrument insertion port 41 of the dome type seal 92, which allows the dome type seal to be moved while the close contact state of the instrument insertion port 41 is maintained.

Then, the airtight structure unit 44 is obtained by bringing the first small diameter portion 37b provided on the distal end side of the airtight rubber cover 37 constituting the seal unit 60 into close contact with the near side surface of the flange 8a of the duckbill valve 8. At this point, as illustrated in FIG. 6, the airtight structure unit 44 is inserted in the head inner cylinder 32, the flange 8a of the duckbill valve 8 is engaged with the stepped portion 32a formed on the inner surface of the head inner cylinder 32, and the plug member 40 is fitted in the head inner cylinder 32 from the near side.

At this point, the distal end surface 40a (see FIG. 5) of the plug member 40 abuts on the projection edge 93d of the dome type seal fixing near side mount 93, and abutment force is transmitted to the dome type seal fixing near side mount 91 through the pin 91c caulked by heat, and transmitted to the first small diameter portion 37b provided on the distal end side of the airtight rubber cover 37 through the distal end side (remote position side end edge 42d) of the seal holder 42 abutting on the dome type seal fixing near side mount 91, and the distal end surface 40a can be brought into close contact with the near side surface of the flange 8a of the duckbill valve 8.

Consequently, the four components are integrally pressed against the flange 8a of the duckbill valve 8, whereby the duckbill valve 8 and the dome type seal 92 are coupled together in an airtight state.

In the embodiment, the airtight structure unit 44 has the structure in which the seal unit 60 and the duckbill valve 8 are brought into close contact with each other. Alternatively, the seal unit 60 and the duckbill valve 8 may be integrated with each other using the airtight rubber cover 37 of the seal unit 60. That is, the airtight rubber cover 37 and the duckbill valve 8 may be joined or integrally molded.

<Camera>

The camera 5 can be stored inside the pipe 2 as described later, and is deployed outward from the outer circumferential surface of the pipe 2 in the abdominal cavity. FIGS. 2 and 3 illustrate a deployment state and a storage state of the camera 5 in the trocar 1, respectively. FIGS. 4A and 4B illustrate a state in which the trocar shaft 4 is pulled out from the trocar 1 while the camera 5 is deployed.

Figure 11A:
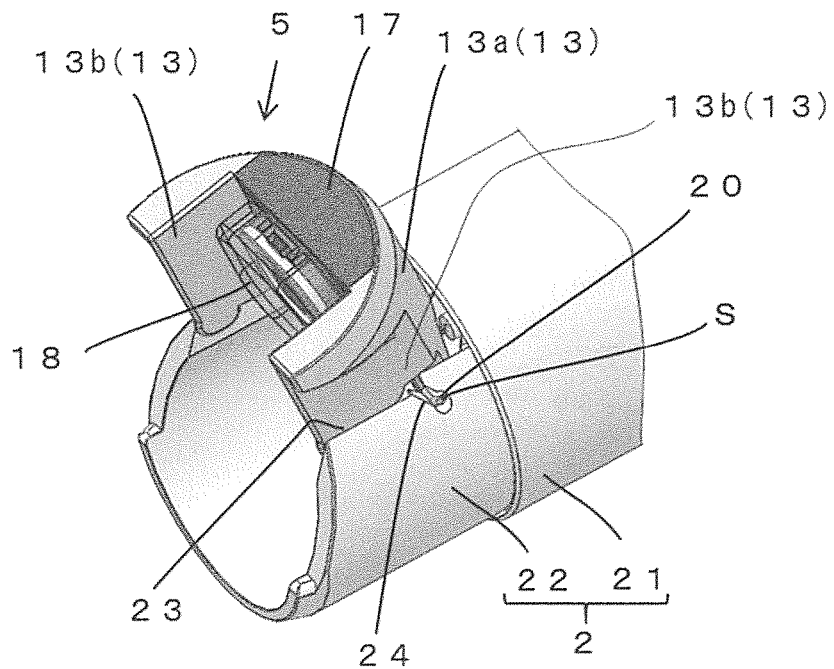
FIG. 11A is a perspective view illustrating a distal end of the trocar in a camera deployment state.
Figure 11B:
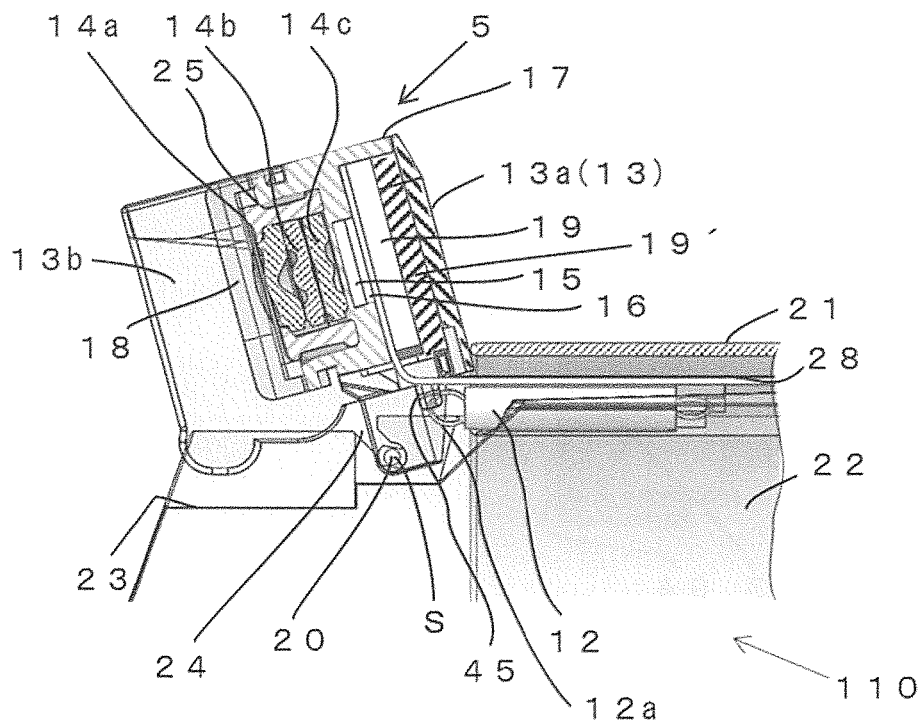
FIG. 11B is a sectional view illustrating the distal end of the trocar in the camera deployment state.

FIGS. 11A and 11B are enlarged views of the distal end in FIGS. 4A and 4B, and the camera 5 is deployed to the outside of the pipe 2. Both ends of the camera 5 are turnably journaled such that the camera 5 can be accommodated in a distal end notch 23 of the inner cylinder 22. Consequently, the camera 5 can freely turn between a deployment state in which the camera 5 is turnable to the outside of the pipe 2 while being capable of photographing and a storage state in which the camera 5 is stored inside the pipe 2. Since the camera 5 in the deployment state is located at the distal end of the inner cylinder 22, a field of view is not blocked by the pipe 2, and the camera 5 in the deployment state is suitable for photographing a surgical field.

That is, the camera 5 includes a substantially U-shaped housing 13 and an imaging unit 17 attached to a front surface (in the embodiment, a U-shaped inner bottom surface) of the housing 13, and light Lenses 14a, 14b, and 14c, an imaging sensor protecting light transmitting plate 15, and an imaging sensor 16 (CMOS or the like) are attached to the imaging unit 17 in the order along a light transmission direction. The lenses 14a, 14b, 14c are stacked in the lens barrel 25.

A flexible cable 28 is connected to the imaging sensor 16. The flexible cable 28 passes through a gap between the outer cylinder 21 and the inner cylinder 22, passes through a gap between the head outer cylinder 31 and the head inner cylinder 32, which are connected to the outer cylinder 21 and the inner cylinder 22, respectively, is drawn out to the outside of the head 3 from a near side single edge of the head outer cylinder 31, is drawn in the connector 11 through an opening (not illustrated) formed in the surface on the side of the head 3 of the connector 11, and is connected to a circuit board 100 (see FIG. 5) (to be described later). A translucency protective cover 18 is attached to the front surface of the lens 14a.

Although the lenses 14a, 14b, 14c and the imaging sensor protecting light transmitting plate 15 can be made of optical glass or optical resin, but the lenses 14a, 14b, 14c and the imaging sensor protecting light transmitting plate 15 are preferably made of a resin material, which can be manufactured at low cost and easily formed into an aspheric surface.

Details of an optical system including the lenses 14a, 14b, 14c and the imaging sensor protecting light transmitting plate 15 will be described later.

Figure 15A:
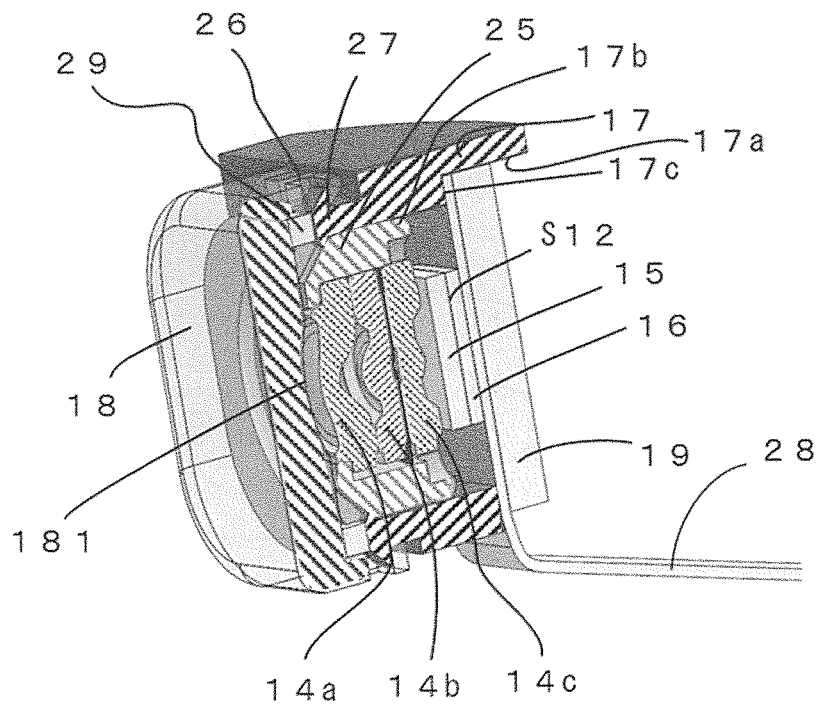
FIG. 15A is a broken perspective view illustrating a structure of the camera.

An imaging sensor reinforcing metal plate 19 (back plate) is disposed on a back side of the flexible cable 28 connected to the imaging sensor 16. The imaging sensor reinforcing metal plate 19 is directly mounted on the flexible cable 28, so that the imaging sensor reinforcing metal plate 19 maintains planarity of the imaging sensor 16 and protects the imaging sensor 16. An aluminum plate which also has a heat radiation effect of the imaging sensor 16 is preferably used as the imaging sensor reinforcing metal plate 19. As illustrated in FIG. 15A, the imaging sensor 16 directly mounted on the flexible cable 28 reinforced by the imaging sensor reinforcing metal plate 19 is inserted through a rear opening 17a of the imaging unit 17, and the flexible cable 28 including the imaging sensor is adhered and fixed to the stepped (flat surface) portion 17c formed at a boundary with the small diameter cylinder 17b on which the lens barrel 25 is mounted, and the imaging sensor 16 including a protective cover 18 on its surface is positioned and fixed on the imaging unit 17. The gap between the imaging sensor reinforcing metal plate 19 and the housing 13 is sealed with a filling material 19' such as a silicone material (FIG. 11B).

The housing 13 includes a curved rear surface 13a that is the same surface as the inner cylinder 22 in the storage state of the camera 5, and side surfaces 13b are formed on both sides of the rear surface 13a. The rear surface 13a is formed into the curved shape as described above, so that the outer cylinder 21 can slide smoothly during the storage and deployment of the camera 5. In the deployment state of the camera 5, the lenses 14a, 14b, 14c face the front of the pipe 2. The inner surface of the housing 13 also functions as a hood of the lens 14 of the camera 5, so that part of illumination light of the laparoscope can be blocked so as not to enter the lens 14 of the camera 5 as stray light during the operation.

Figure 14:
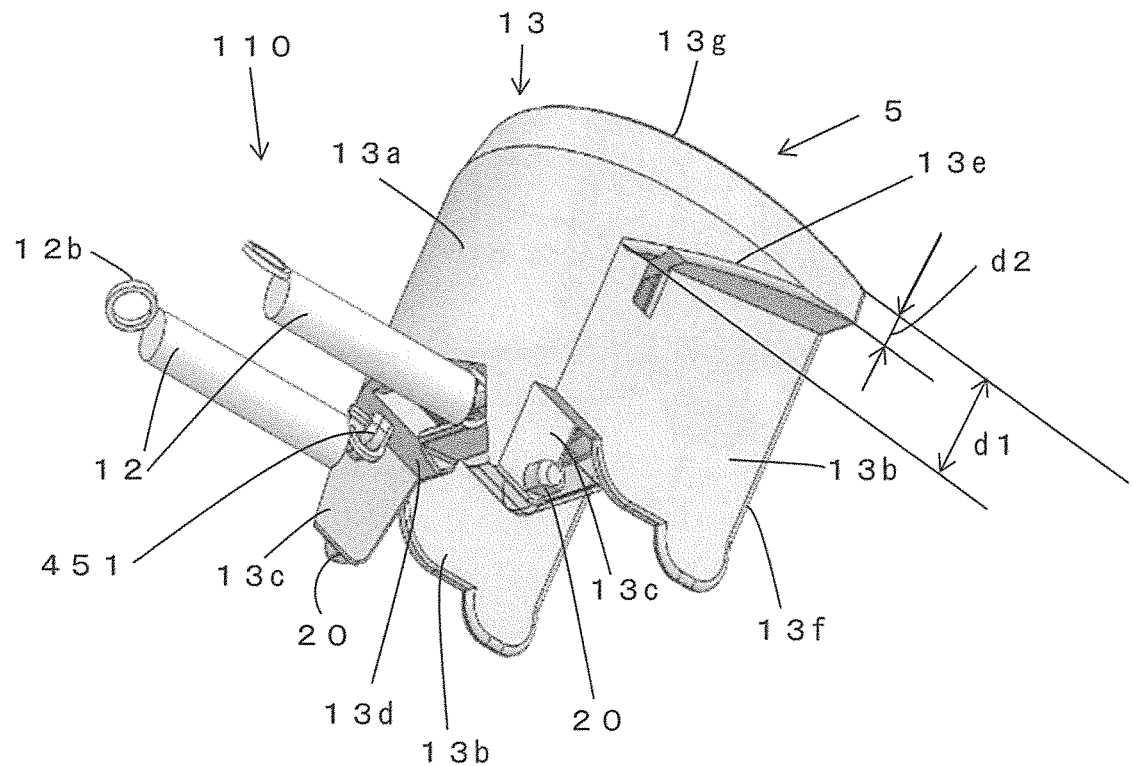
FIG. 14 is a perspective view illustrating a rotation mechanism of the camera.

Referring to FIG. 14, a slope 13e is provided adjacent to the side surface 13b in the upper portion in the drawing of the housing 13 (the remote position of the trocar in the camera storage state). The slope 13e is formed such that a width from the side of the rear surface 13a to a remote end side 13g toward an end edge 13f of the side surface 13b is narrowed (d1>d2). This is a structure that enables the slope 13e to be brought into contact with a slope 22e (see FIG. 2A) provided at the remote end (distal end) of the inner cylinder 22 when the camera is accommodated. Also, in the structure, the corner is formed into an obtuse angle such that the contact surface between the housing and the inner cylinder is easily secured when the camera is swung and accommodated, and the camera 5 is securely held by securing a contact surface area at the same time.

A camera holding mechanism and a deployment and storage mechanism 110 of the present disclosure will be described with reference to FIGS. 11 to 14.

Figure 12:
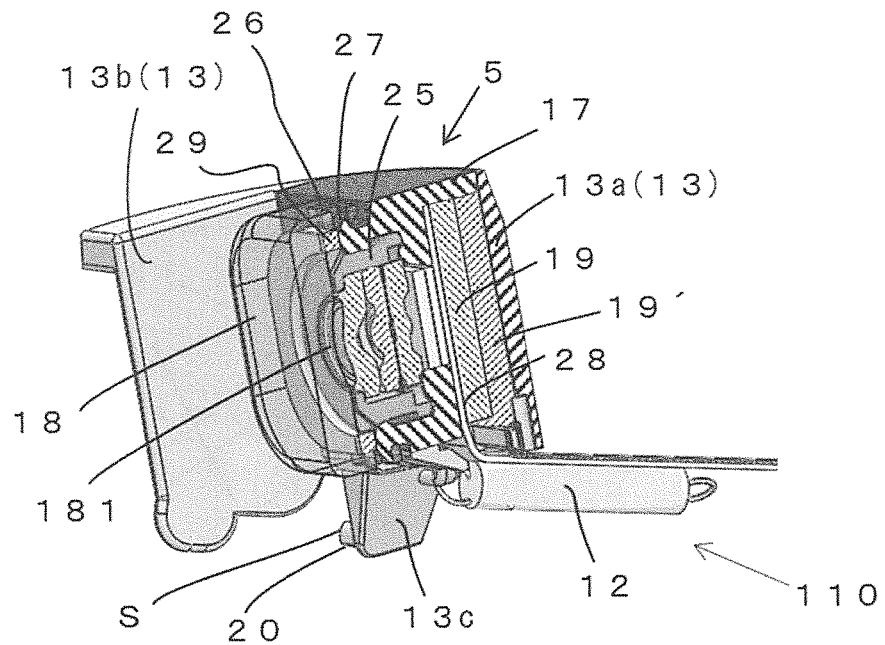
FIG. 12 is a sectional view illustrating a camera.
Figure 13:
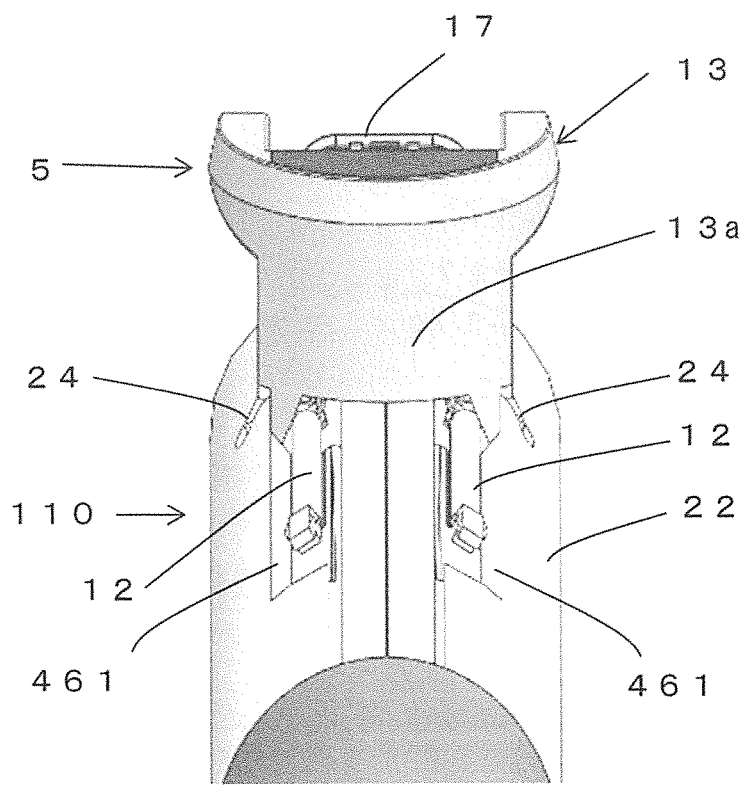
FIG. 13 is a perspective view illustrating the distal end of the trocar in the camera deployment state when viewed from a proximal side (near side).

As illustrated in FIGS. 12 and 13, a projection 13c extending downward in the inner cylinder 22 is formed at a lower end in each of both side surfaces 13b, 13b of the housing 13, and a shaft 20 is formed in each projection 13c so as to project in an outward direction orthogonal to an axial direction of the pipe 2.

As illustrated in FIGS. 11A, 11B, and 13, the shaft 20 is inserted through a slope groove 24 cut obliquely from both sides of the distal end notch 23 of the inner cylinder 22 toward the near side, and engaged with the slope groove 24. The center of the shaft 20 acts as a pivot point S at which the camera 5 is turned. Consequently, in spite of a compact size, moment can be secured when the camera 5 is tilted down using pulling force of a coil spring 12 (elastic member) (to be described later). The camera 5 is easily attached because the slope groove 24 is adopted as described above.

As illustrated in FIG. 14, L-shaped portions 451 project downward from both sides of the bottom 13d of the housing 13, and a ring-shaped portion 12a located at one end of the coil spring 12 is engaged with the L-shaped portion 451. As illustrated in FIG. 13, the two coil springs 12 are accommodated in a recessed groove 461 extending along the axial direction of the pipe 2 from the distal end notch 23 of the inner cylinder 22 to the near side (proximal side), and the ring-shaped portion 12b at the other end on the near side of the coil spring 12 is fixed into the recessed groove 461.

One end (ring-shaped portion 12a) of the coil spring 12 is engaged on the near side of the shaft 20 and at a position radially outward of the pipe 2 from the shaft 20. Consequently, the camera 5 is biased to the near side. Consequently, the camera 5 is turned backward about the pivot point S, and is in the deployment state.

For this reason, when the trocar 1 is pulled out from the body with the camera 5 deployed inside the body, the axial direction of the pipe 2 is turned by external force applied from the rear end side to the distal end side in pulling out the trocar, and the camera 5 is safely stored in the inner cylinder 22.

In particular, when large unexpected force acts on the camera 5 from the rear end side to the distal end side, the L-shaped portion 451 is configured to be disengaged from the ring-shaped portion 12a at one end of the coil spring 12, and the shaft 20 is engaged with the slope groove 24 of the inner cylinder 22. Consequently, the shaft 20 is separated so as to slide along the slope groove 24, and the camera 5 can be detached. Thus, in the case of emergency or the like, the camera 5 can be separated from the trocar 1 without damaging the camera 5, the safety can be improved, and a damage risk of the camera 5 can be reduced.

At this point, since the other end of the coil spring 12 is fixed, the coil spring 12 does not fall into the abdominal cavity.

In the embodiment, in order to reduce the size of the camera 5 as much as possible, the imaging sensor 16 is directly mounted on the flexible cable 28. This mounting portion does not have a controller function of controlling the imaging sensor 16, and the controller function such as clock control is disposed in the circuit board 100 (control means, see FIG. 5) provided in the head 3. Thus, the end of the flexible cable 28 directly mounted on the imaging sensor 16 is connected to the circuit board 100 in the connector 11 of the head 3, and an image signal is sent out to the outside through an external cable 102 (USB cable) soldered from the circuit board 100.

Figure 15B:
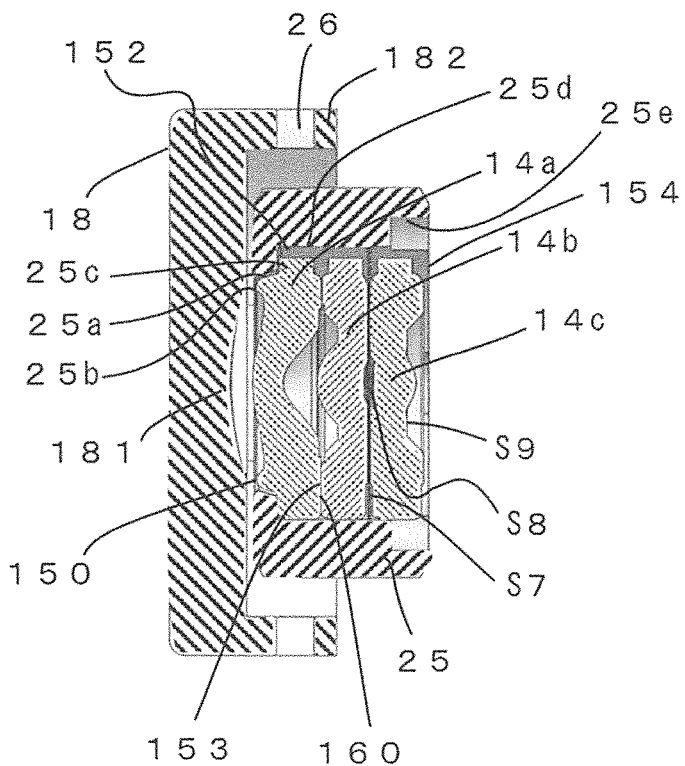
FIG. 15B is a sectional view illustrating a lens optical system.

In the case that the translucent protective cover 18 is made of a transparent optical resin, as illustrated in FIGS. 15A and 15B, the inner surface adjacent to the lens 14a constitutes a concave curved surface 181 and has optical performance. Since the translucent protective cover 18 exerts the function of the lens, the number of lenses to be used can be decreased, the distance between the translucent protective cover 18 and the lenses 14a, 14b, 14c can be decreased, and the thickness and size of the camera 5 can be reduced. A structure such as a peripheral wall (to be described later) can integrally be molded.

The translucent protective cover 18 includes a circumferential wall 182, and a hole 26 is made in the circumferential wall 182. On the other hand, the imaging unit 17 includes a claw 27 on the distal end side, and the claw 27 is engaged with the hole 26 to integrate the translucent protective cover 18 with the imaging unit 17 during the attachment of the translucent protective cover 18. At that point, in order to ensure a waterproof property, a sealing member 29 such as rubber is fitted between the imaging unit 17 and the translucent protective cover 18. Consequently, the camera 5 has a watertight structure, and is suitably used in the body wall.

<Lock Mechanism (1)>

Figure 16A:
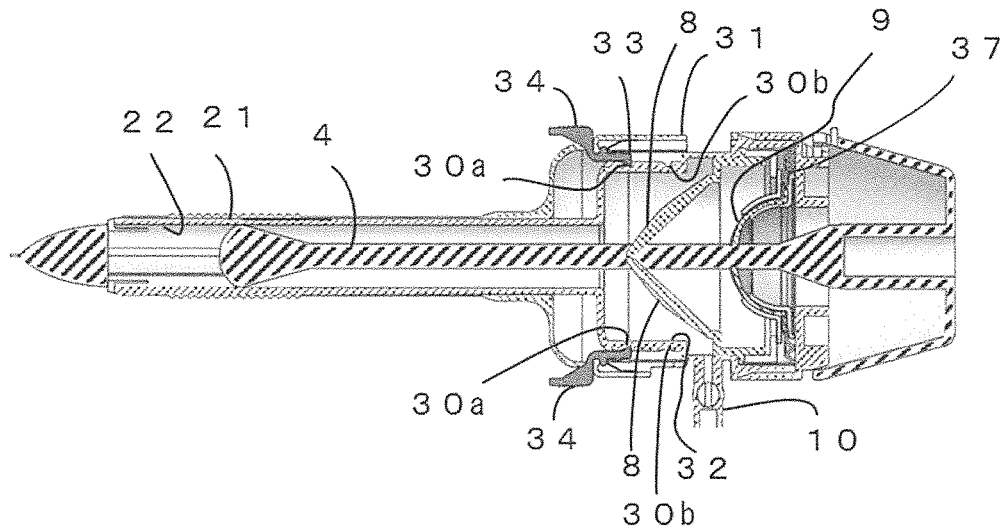
FIG. 16A is a sectional view illustrating operation of a outer cylinder in the camera storage state.
Figure 16B:
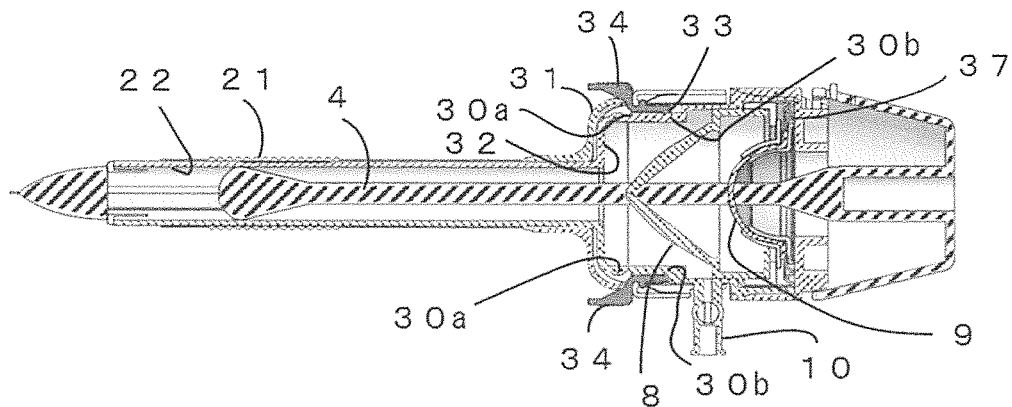
FIG. 16B is a sectional view illustrating the operation of the outer cylinder in the camera deployment state.

A lock mechanism that holds the camera 5 in the deployment state or the storage state to prevent the camera 5 from inadvertently operating will be described below. FIGS. 16A and 16B are sectional views obtained by rotating the sectional views of FIG. 3B illustrating the storage state and FIG. 2B illustrating the deployment state by 90°, respectively.

As illustrated in FIGS. 16A and 16B, two recesses 30a, 30b are arranged in the axial direction on the outer circumferential surface of the head inner cylinder 32 to which the inner cylinder 22 is connected. On the other hand, a lock lever 34 including a claw-shaped protrusion 33 is attached to the head outer cylinder 31 to which the outer cylinder 21 is connected.

The pair of recesses 30a, 30b and the lock lever 34 are provided in pairs at positions having 180-degree symmetry.

In the storage state (FIG. 16B) of the camera 5, the protrusion 33 provided at the distal end of the lock lever 34 is engaged with the recess 30a on the distal end side to lock the outer cylinder 21. On the other hand, in the deployment state (FIG. 16B) of the camera 5, the protrusion 33 is engaged with the recess 30b on the near side to lock the outer cylinder 21. These operations can be performed by the lock lever 34 extending from the head outer cylinder 31 to the outside. That is, by pushing one end exposed to the outside of the lock lever 34 with a finger, the protrusion 33 provided at the other end of the lock lever 34 is turned upward to be separated from the recess 30a or 30b, and the outer cylinder 21 is slid in this state.

The outer cylinder 21 is formed so as to be shorter than the inner cylinder 22 in length. This is because the outer cylinder 21 is located behind the camera 5 in the state (the state in FIG. 16B) in which the camera 5 is deployed to the outside of the pipe 2 from the distal end notch 23 of the inner cylinder 22.

Figure 17A:
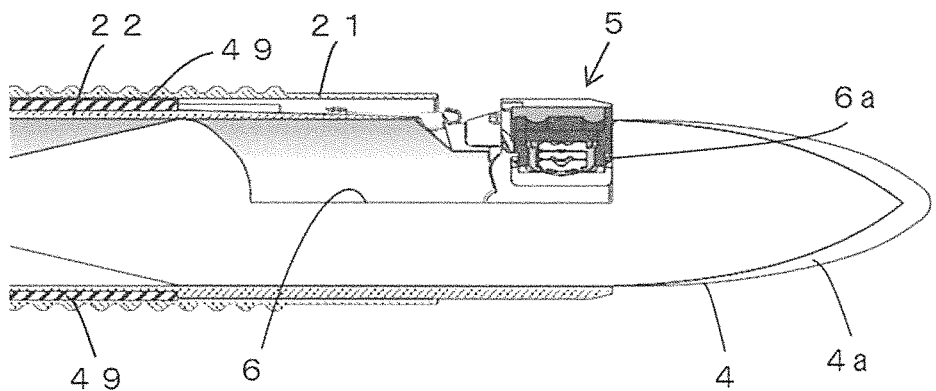
FIG. 17A is a schematic diagram illustrating a lock mechanism of the camera by the trocar shaft.
Figure 17B:
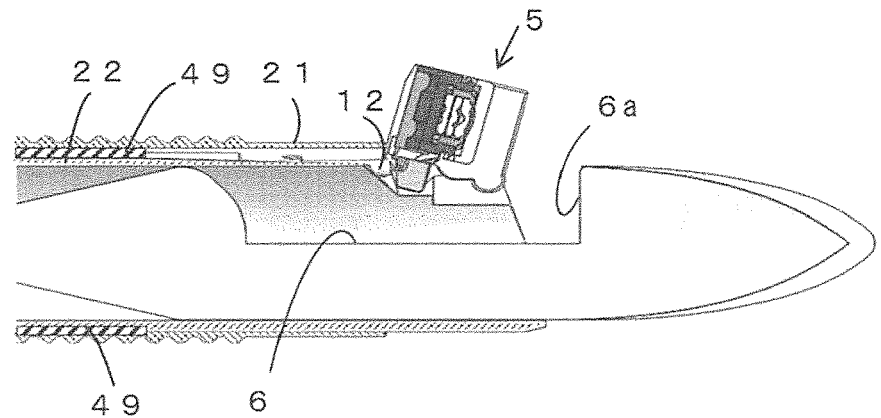
FIG. 17B is a schematic view illustrating the lock mechanism of the camera by the trocar shaft.

As illustrated in FIGS. 17A and 17B, a tubular sealing member 49 is interposed between the outer cylinder 21 and the inner cylinder 22. The tubular sealing material 49 is made of silicone rubber or the like, and packages the inner cylinder 22 so as to sandwich the flexible cable 28. Even in presence of the flexible cable 28, the outer cylinder 21 can be slid while the tubular sealing member 49 maintains the airtight state. In order to reduce a friction coefficient of the tubular sealing member 49, lubricating action may be ensured by oils and fats, such as silicone oil, which are usable for medical use.

<Lock Mechanism (2)>

In the embodiment, the camera 5 is locked by the trocar shaft 4 such that the camera 5 is not unintentionally deployed in the storage state of the camera 5. That is, as illustrated in FIG. 17A, in the state in which the camera 5 is accommodated in the notch 6 formed in the trocar shaft 4, the distal end surface of the camera 5 abuts on the distal end wall 6a of the notch 6 to prevent the camera 5 from turning. Thus, the lock state can surely be maintained in cooperation with the lock mechanism of the lock lever 34.

On the other hand, in order to release the lock of the trocar shaft 4, the camera 5 can easily be deployed when a gap is formed between the distal end wall 6a of the trocar shaft 4 and the distal end surface of the camera 5 as illustrated in FIG. 17B.

Figure 18:
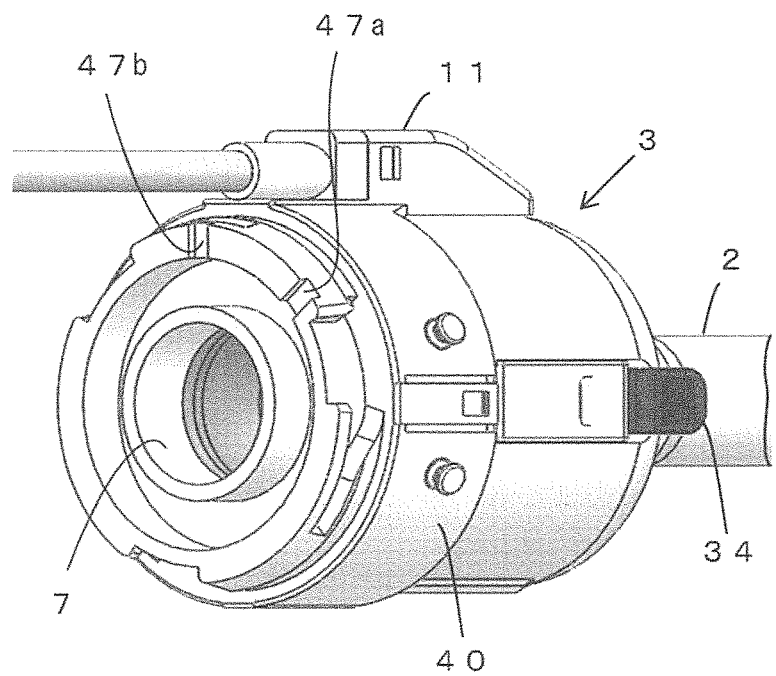
FIG. 18 is a perspective view illustrating a form of a plug member.

In order to lock and release by the trocar shaft 4, as illustrated in FIG. 18, a camera storage position click groove 47a and a camera deployment position click grooves 47b are arranged at a predetermined interval in the outer circumferential portion of the end face of the plug member 40 located on the near side (proximal side) of the trocar 1. When the trocar shaft 4 is inserted in the opening 7 of the plug member 40 to attach the handle portion 4b to the end face of the plug member 40, a projection (not illustrated) provided in the handle 4b is engaged with the camera storage position click groove 47a in the storage state of the camera 5. On the other hand, during the deployment, the handle 4b is held to turn the trocar shaft 4, and the protrusion is engaged with the camera deployment position click groove 47b. Consequently, a gap D is formed between the distal end wall 6 of the trocar shaft 4 and the distal end surface of the camera 5 (see FIG. 19B), and the camera 5 can be deployed.

That is, the camera deployment position click groove 47b is deeper than the camera storage position click groove 47a, so that the trocar shaft 4 can be moved onto the distal end side to form the gap D with the distal end surface of the camera 5.

A method for using the trocar 1 of the embodiment will be described below with reference to FIGS. 19A to 19D. The trocar shaft 4 is turned from the camera storage position click groove 47a to the camera deployment position click groove 47b in an initial state (the storage state of the camera 5) of FIG. 19A, and the gap D is formed between the distal end wall 6 of the trocar shaft 4 and the distal end surface of the camera 5 (FIG. 19B).

Figure 19A:
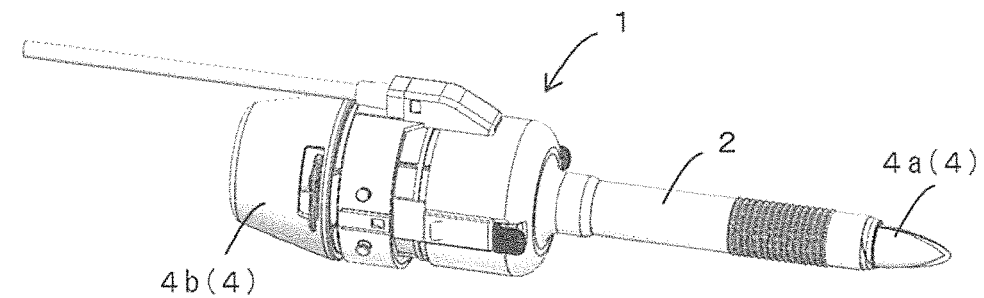
FIG. 19A is a perspective view illustrating a method for using the trocar.
Figure 19B:
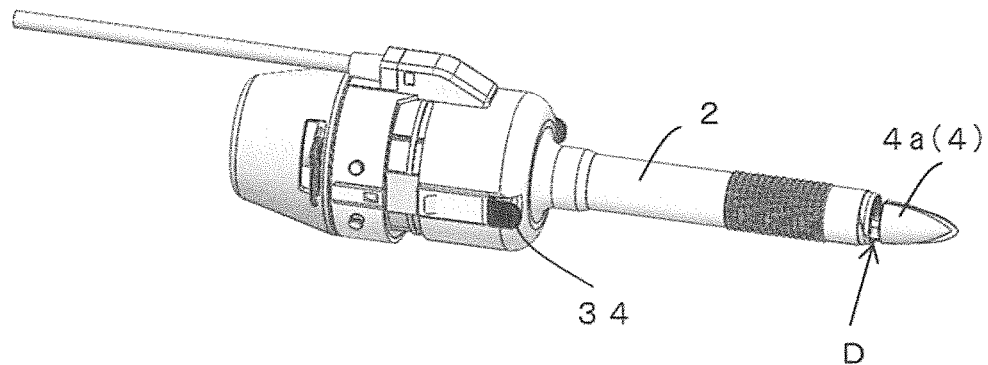
FIG. 19B is a perspective view illustrating the method for using the trocar.
Figure 19C:
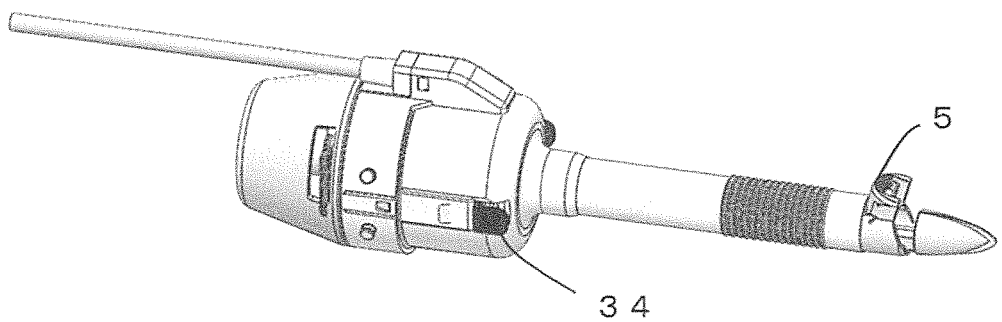
FIG. 19C is a perspective view illustrating the method for using the trocar.

Then, as illustrated in FIG. 19C, the lock lever 34 of the outer cylinder 21 is pushed to slide the outer cylinder 21 toward near side. Consequently, the camera 5 is deployed by the biasing force of the coil spring 12 (see FIG. 11), and the trocar shaft 4 can be pulled out.

Figure 19D:
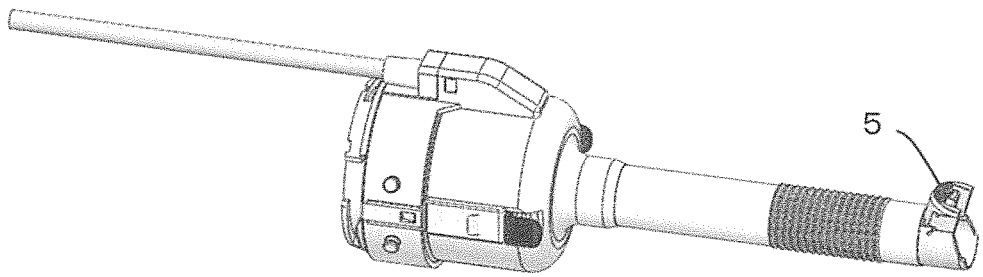
FIG. 19D is a perspective view illustrating the method for using the trocar.

At this point, as illustrated in FIG. 19D, the trocar shaft 4 can be pulled out and used as a trocar port.

Figure 20:
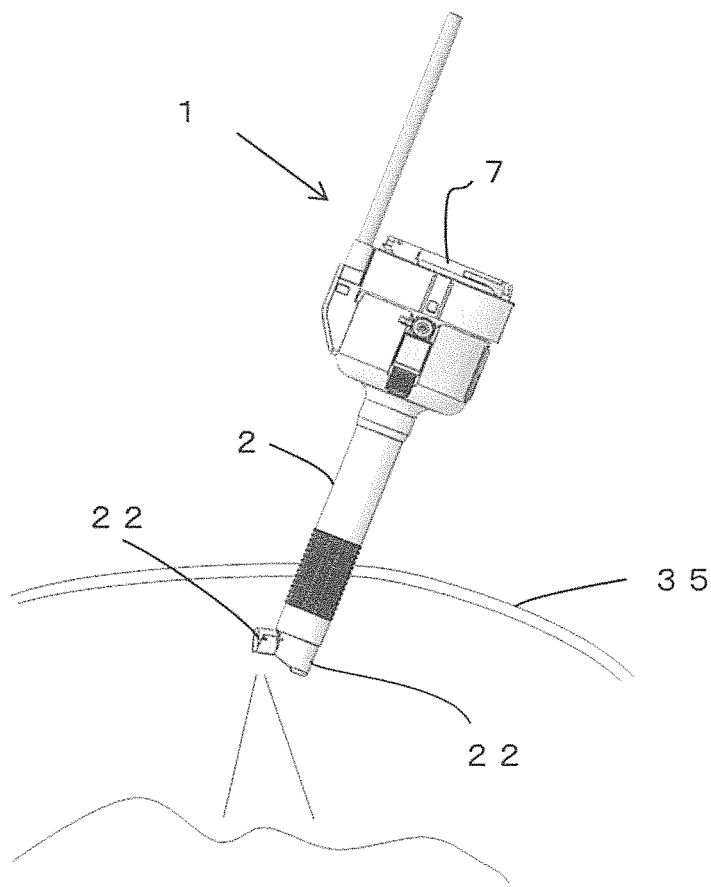
FIG. 20 is an explanatory diagram illustrating a use state of the trocar.

In actual use, in the initial state (the storage state of the camera 5) of FIG. 19A, the abdominal cavity is punctured through the body wall by the puncture portion 4a formed at the distal end of the trocar shaft 4. Then, the camera 5 is deployed in the body wall 35 as described above, the trocar shaft 4 is pulled out from the trocar 1, and the operation is performed while a stem 36 in the abdominal cavity is photographed as illustrated in FIG. 20.

Thus, while watching the image displayed on the monitor (not illustrated), the operator can perform surgery by inserting the forceps (not illustrated) from the opening 7 of the trocar 1, so that the visual field can be enlarged to facilitate the operation and safety of the operation can also be improved. In particular, since the camera 5 is provided at the distal end of the pipe 2, there is an advantage that the visual field is not disturbed by the pipe 2 and the like.

In storing the camera, a reverse procedure is performed. Specifically, after the trocar shaft 4 is inserted in the trocar 1 to form the gap D between the trocar shaft 4 and the distal end surface of the camera 5, the camera 5 is accommodated, and then the gap D is closed. That is, in order to accommodate the camera 5, the slope 13e of the housing 13 and the remote end slope 22e of the inner cylinder are brought into surface contact with each other, and the outer cylinder 21 is slid to an original position.

<Lens Optical System>

Figure 15C:
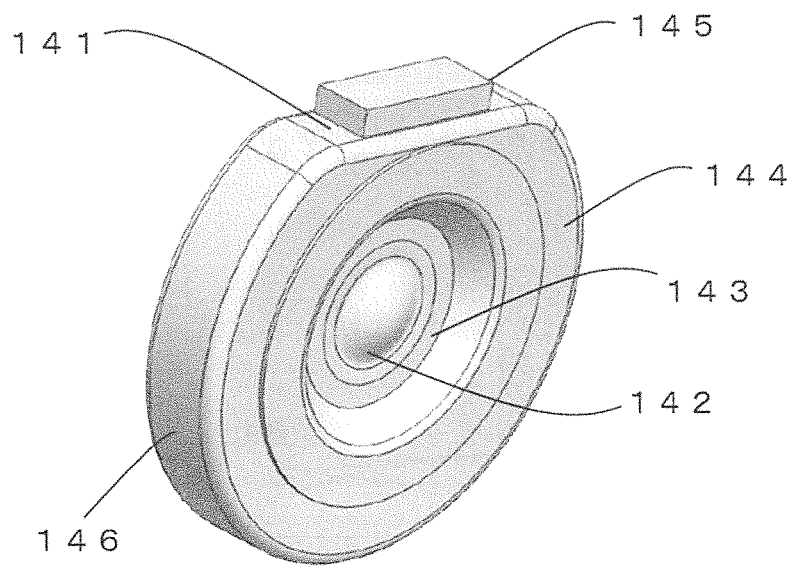
FIG. 15C is a perspective view illustrating a lens L4 constituting the lens optical system.

The lens optical system including the lenses 14a, 14b, 14c and the translucent protective cover 18 will be described below with reference to FIGS. 15A, 15B, 15C. In the embodiment, the optical system includes a plano-concave lens (first lens L1 having negative power) having the function of the translucent protective cover 18, a meniscus concave lens 14a (a second lens L2 having negative power) including a convex surface on an object side, a meniscus convex lens 14b (a third lens L3 having positive power) including a convex surface on the object side, and a biconvex lens 14c (a fourth lens L4 having positive power) in order from the object side (from the left side in FIG. 15B). A stop S7 is provided between the third lens L3 and the fourth lens L4.

In the first lens L1, the image surface side is constructed with a concave surface, and the concave surface is constructed with a spherical surface. In all of the second to fourth lenses, both sides are constructed with aspherical surfaces. Since an imaging surface S12 of the imaging sensor 16 is protected by the imaging sensor protecting light transmitting plate 15, the optical system 14 forms an image of the subject on the imaging surface S12 through the imaging sensor protecting light transmitting plate 15.

In the embodiment, as illustrated in FIGS. 23 to 29 described in Examples (to be described later), surfaces constituting the lens optical system 14 are sequentially referred to as S1, S2, ..., S12 in the order from the surface on the object side of the translucent protective cover 18 to a light reception surface of the imaging sensor 16.

The first lens L1 has the function as the translucent protective cover 18. The object side surface S1 is formed as a flat surface, the image side surface S2 is formed as a spherical surface, and the first lens L1 constitutes a plano-concave lens as a whole. As described above, the first lens L1 includes the circumferential wall 182, and the hole 26 made in the circumferential wall 182 is engaged with the claw 27 of the imaging unit 17 so as to be integrated and assembled.

Consequently, in order to exhibit the optical performance as the first lens L1, it is necessary to originally perform high-accuracy assembly. However, in the present example, in order to adopt such a simple assembling mechanism, the object side surface S1 is formed into the flat surface, and the image plane side S2 is formed into the spherical surface, so that a tolerance during the assembly can be absorbed in relation to the second lens L2 to the fourth lens L4 which are described below.

The second lens L2 to the fourth lens L4 will be described below. These three lenses are resin lenses in each of which an aspherical surface is formed on both sides, and appearances of the three lenses have the shape in FIG. 15C with the fourth lens L4 as a representative. Specifically, the fourth lens L4 has a substantially D-shaped exterior shape including a linear portion 141. A lens portion 142 is formed in the center, and a flange 144 including a flat portion 143 is formed around the lens portion 142. The linear portion 141 includes a gate 145 through which resin is injected into a lens mold during molding.

By forming the flange 144 around the lens portion 142 of the fourth lens L4, the three lenses can be formed into substantially the same outer diameter and outer circumferential shape. In addition, surface spacings of the respective lenses can be accurately uniformed by overlapping three lenses using the flat portion 143 of the flange portion 144.

The assembly of the second lens L2, the third lens L3, the stop S7, and the fourth lens L4 in the lens barrel 25 will be described with reference to FIG. 15B. The lens barrel 25 has a substantially cylindrical appearance, a screw is formed on the outer circumferential surface, and the lens barrel 25 has a sectional shape as illustrated in FIG. 15B. The sectional shape includes, in the order from the object side, an opening 25a, a slope 25b in which an inner diameter is increased from the opening 25a toward the image plane side, a flat surface 25c, a cylindrical portion 25d having the same inner diameter, and an opening 25e having an inner diameter larger than that of the cylindrical portion 25d.

On the other hand, a flange 152 having a tapered ring 150 extending to the optical surface S3 formed into an aspheric shape is formed on the object surface side of the second lens L2, and the ring 150 is fitted in the slope 25b of the lens barrel 25, and the flange 152 of the lens abuts on the flat surface 25c of the lens barrel 25, so that the second lens L2 can be disposed at a predetermined position.

Then, the third lens L3 is inserted in the lens barrel 25, an object side flange 160 is overlapped on an image plane side flange 153 of the second lens, the stop S7 is inserted, and finally the fourth lens L4 is inserted. The cylindrical portion 25d of the lens barrel is designed to have a length such that a part of a flange outer circumferential surface 146 of the fourth lens L4 is positioned at the opening 25e.

The lenses L2, L3, and L4 are fixed by applying an adhesive 154 to the flange outer circumferential surface 146 of the fourth lens L4 and the opening 25e after the fourth lens L4 is inserted.

The lens barrel 25 in which the lenses L2 and L3, the stop S7, and the lens L4 are assembled is screwed into the imaging unit 17, and the position of the lens barrel 25 is adjusted to the imaging sensor 16 already mounted from the rear opening 17a of the imaging unit 17. The camera is completed by attaching the first lens L1 that also serves as the final protective cover to the imaging unit 17 according to the above-described method.

The materials used for the lenses L1 to L4 will be described. The optical system of the present disclosure is incorporated in the camera 5 incorporated in the trocar 1, and mainly used in the laparoscopic surgery. For this reason, a resin material used in medical applications is desirably used for the first lens L1 directly contacting with the abdominal cavity. By applying a hydrophilic coating to the surface of the first lens L1, even if a body fluid adheres to the surface of the first lens L1, disturbance of imaging performance can be prevented.

On the other hand, the lenses L2, L3, and L4 are made of a resin material having an ordinary optical grade because the first lens L1 functions as the protective cover and has a watertight structure through the sealing member 29 (O-ring).

Optical features will be described below. The lenses L1 to L4 of the embodiment preferably have the following optical features.

(1) Assuming that f is focal length of the first lens L1, and that $f_{234}$ is a composite focal length of the second lens, the third lens, and the fourth lens, the following conditional expression is satisfied.

$$0.80 < f/f_{234} < 0.96 \qquad \text{(Expression 1)}$$

Consequently, distortion (distortion aberration) can effectively be prevented. $f/f_{234}$ is more preferably set to a range of 0.81 to 0.89, thereby more effectively preventing generation of the distortion.

(2) Assuming that f is the focal length of the first lens L1, and that t2 is a spacing on the optical axis between the first lens L1 and the second lens L2, the following conditional expression is satisfied.

$$0.11 < \frac{t_2}{f} < 1.40 \qquad \text{(Expression 2)}$$

Consequently, the distortion (distortion aberration) can effectively be prevented, and a field curvature can be prevented. $t_2/f$ is more preferably set to a range of 0.70 to 1.30, thereby performing more effective correction.

(3) Assuming that $f_2$ is the focal length of the second lens L2, and that $f_{234}$ is the composite focal length of the second lens, the third lens, and the fourth lens, the following conditional expression is satisfied.

$$1.50 < \frac{|f_2|}{f_{234}} < 2.30 \qquad \text{(Expression 3)}$$

Consequently, high resolution can be obtained from a center of the visual field to a periphery of the visual field while a peak value of MTF is enhanced. $|f2|/f_{234}$ is more preferably set to a range of 1.70 to 1.85, thereby performing more effective correction.

Thus, by satisfying these (Mathematical Expression 1) to (Mathematical Expression 3), the lens optical system of the embodiment can secure a wide field angle and provide a stable optical system.

Another Embodiment

Figure 21:
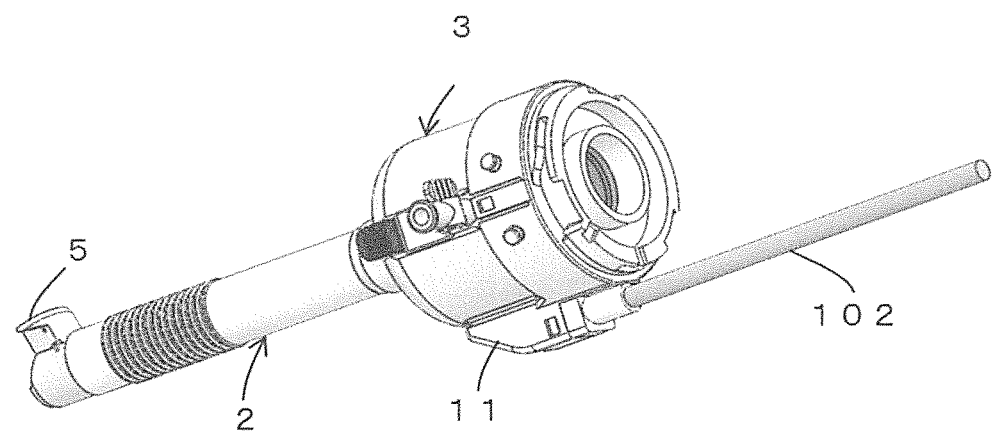
FIG. 21 is a perspective view illustrating a trocar according to another embodiment of the present disclosure.

In the above embodiment, the camera 5 and the connector 11 are disposed on the same side with respect to the pipe 2. Alternatively, the camera 5 and the connector 11 may be disposed at different positions. For example, as illustrated in FIG. 21, the camera 5 and the connector 11 can be disposed at symmetrical positions with respect to an axial center of the pipe 2 or at positions near the symmetrical positions.

In this case, the external cable 102 can be placed below the position of the hand of the operator during the operation, the operator's hand touches the external cable 102 to move the camera 5, and the camera 5 is turned about the pipe 2 as a turning axis, the turning of a projected operating field can effectively be prevented.

The camera 5 and the connector 11 may be disposed at positions different from the mounting position of the camera in the circumferential direction of the head such that the hand of the operator does not touch the external cable 102. For example, the connector 11 may be disposed at an angle of at least 90° from the camera 5 to the left and right with respect to the axial center of the pipe 2.

Other configurations are the same as those in the above embodiment.

Still Another Embodiment

Figure 22A:
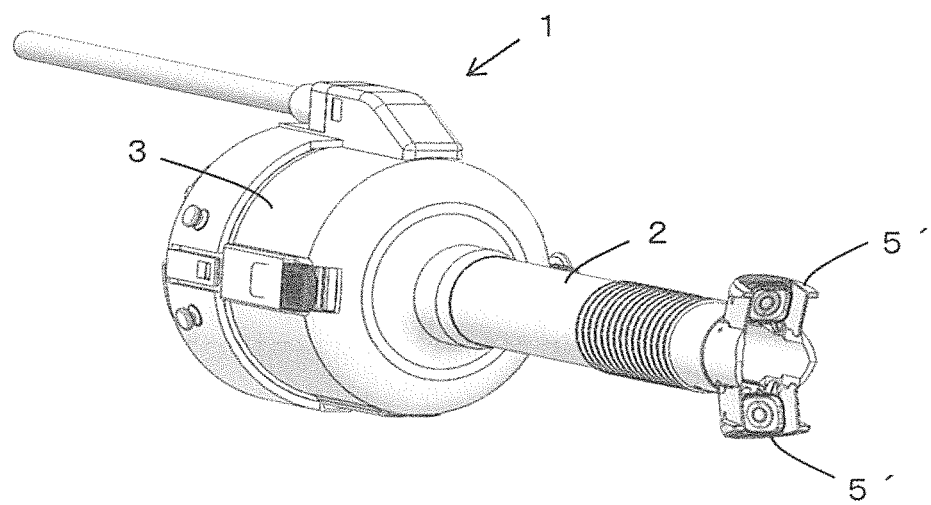
FIG. 22A is a perspective view illustrating a trocar according to still another embodiment of the present disclosure.
Figure 22B:
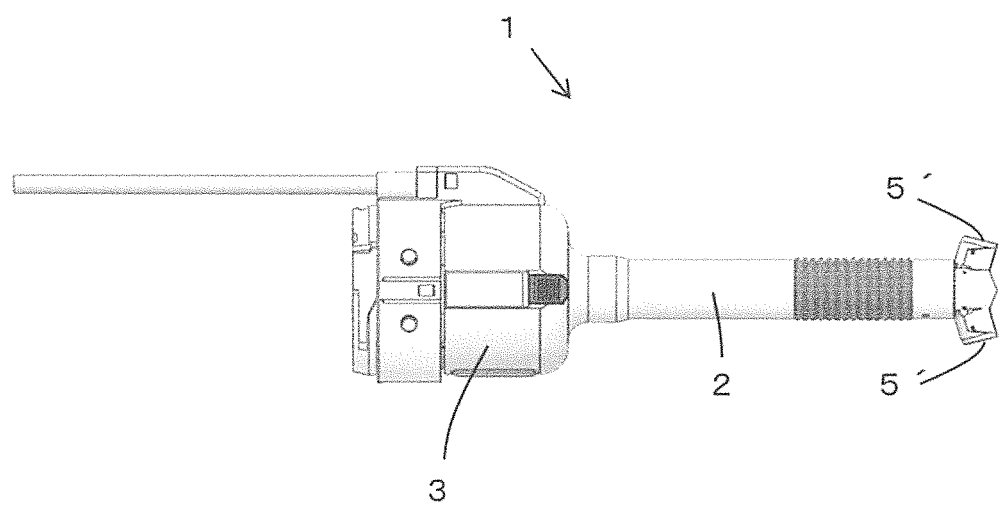
FIG. 22B is a side view illustrating the trocar in FIG. 22A.
Figure 23:
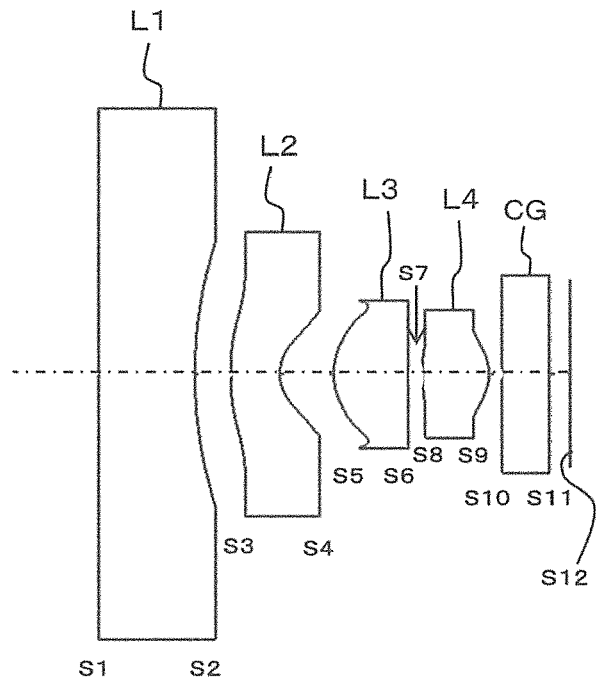
FIG. 23 is an explanatory view illustrating a lens configuration in Example 1.
Figure 24:
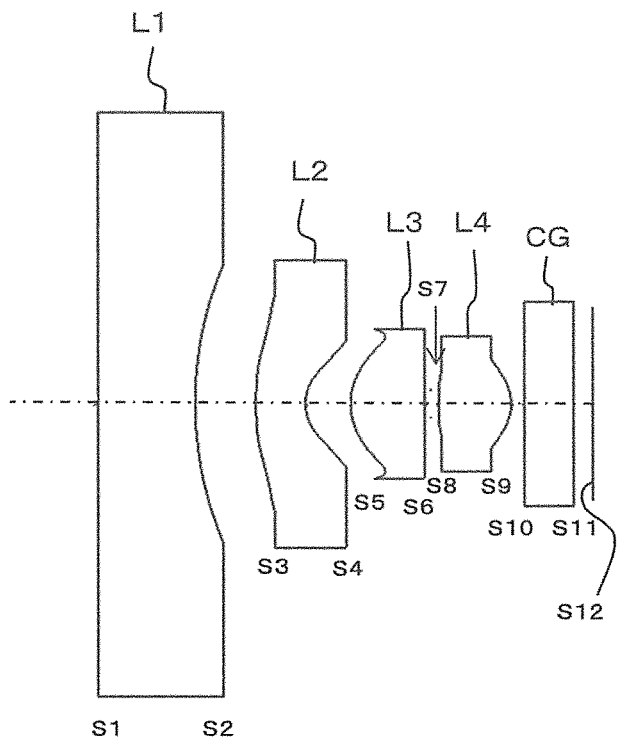
FIG. 24 is an explanatory view illustrating a lens configuration in Example 2.
Figure 25:
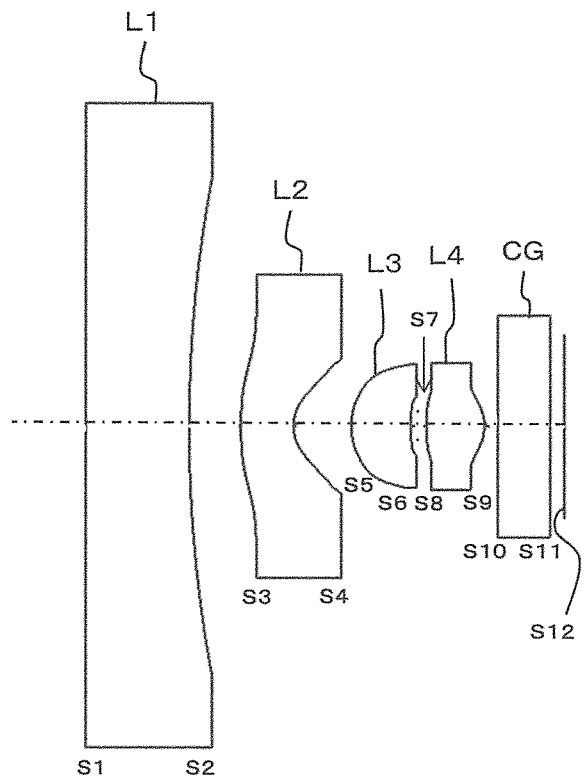
FIG. 25 is an explanatory view illustrating a lens configuration in Example 3.
Figure 26:
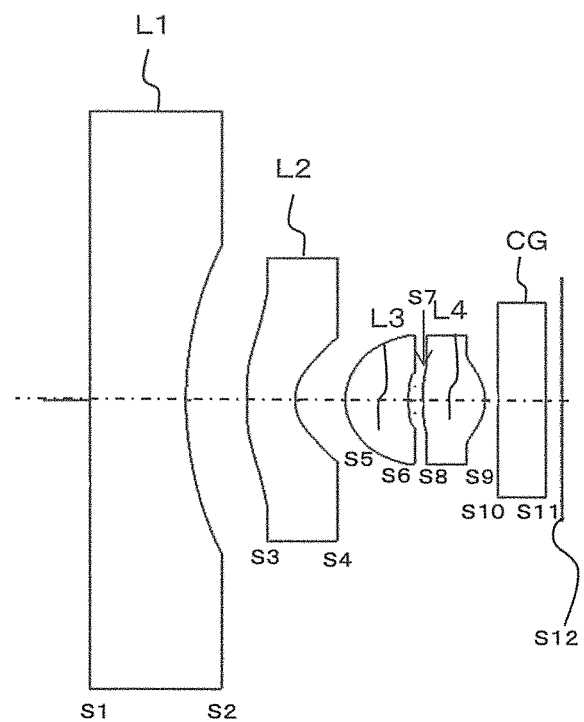
FIG. 26 is an explanatory view illustrating a lens configuration in Example 4.
Figure 27:
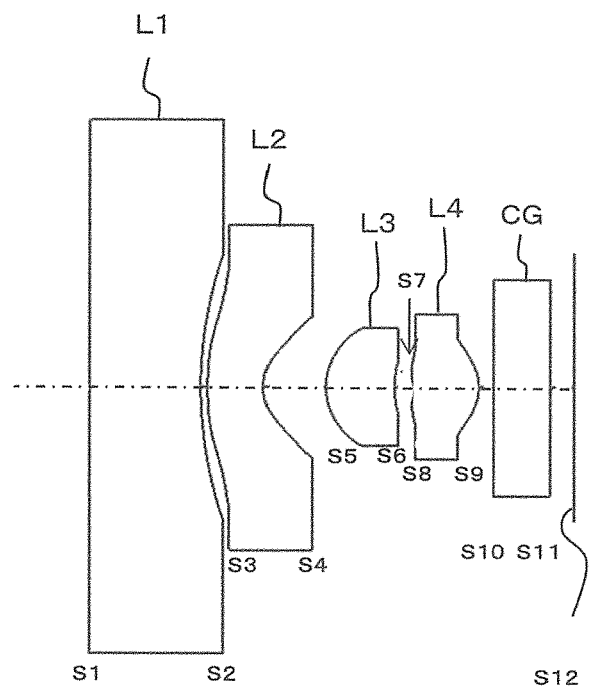
FIG. 27 is an explanatory view illustrating a lens configuration in Example 5.
Figure 28:
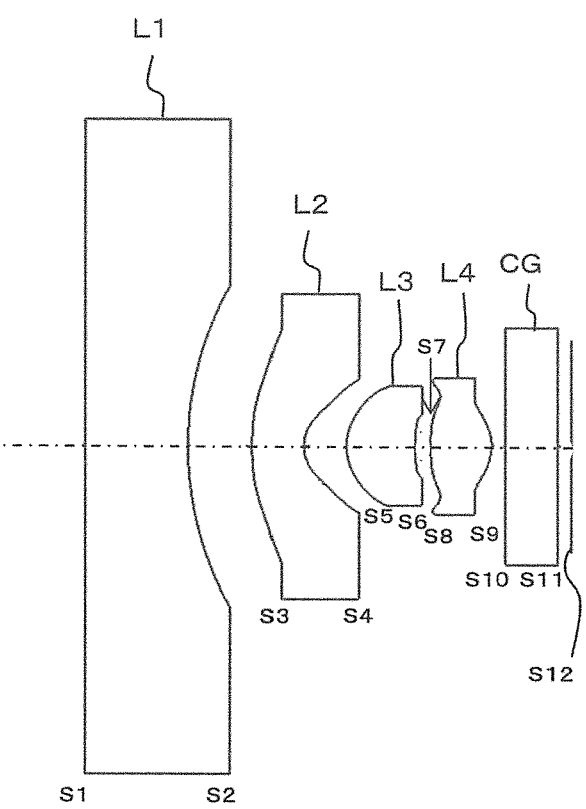
FIG. 28 is an explanatory view illustrating a lens configuration in Example 6.
Figure 29:
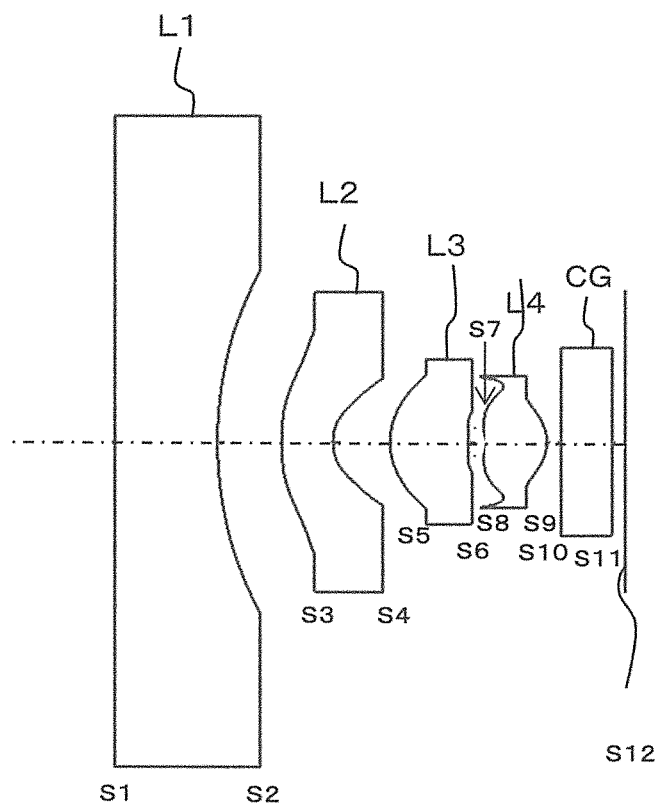
FIG. 29 is an explanatory view illustrating a lens configuration in Example 7.
Figure 30:
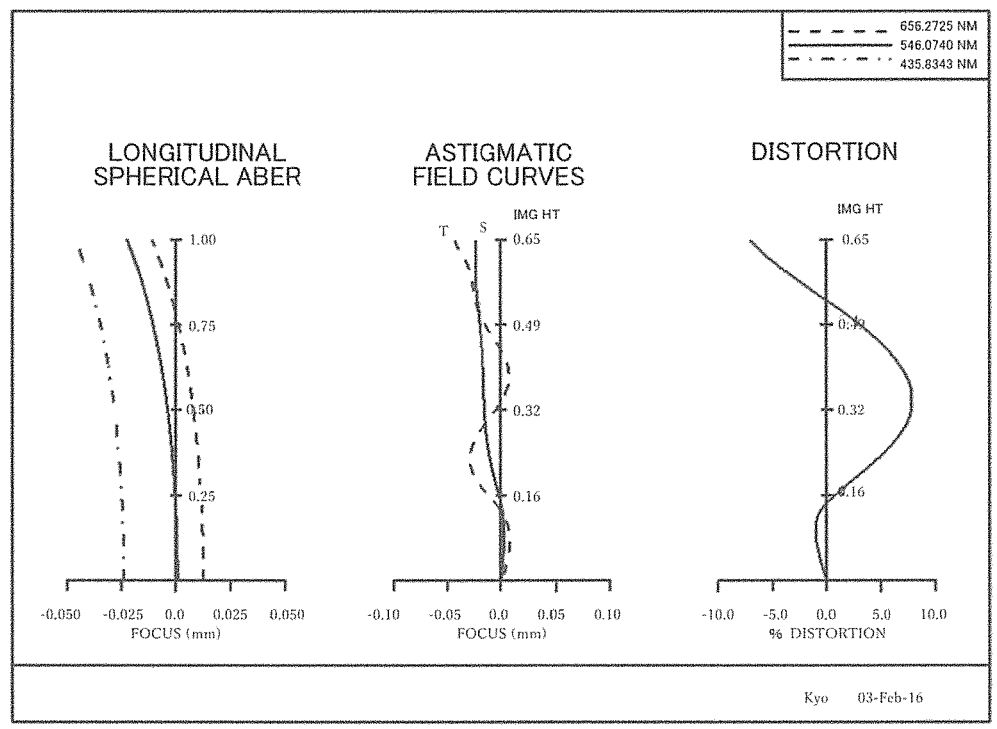
FIG. 30 is a graph illustrating aberration diagrams (spherical aberration, astigmatism, and field curvature) of a lens optical system of Example 1.
Figure 31:
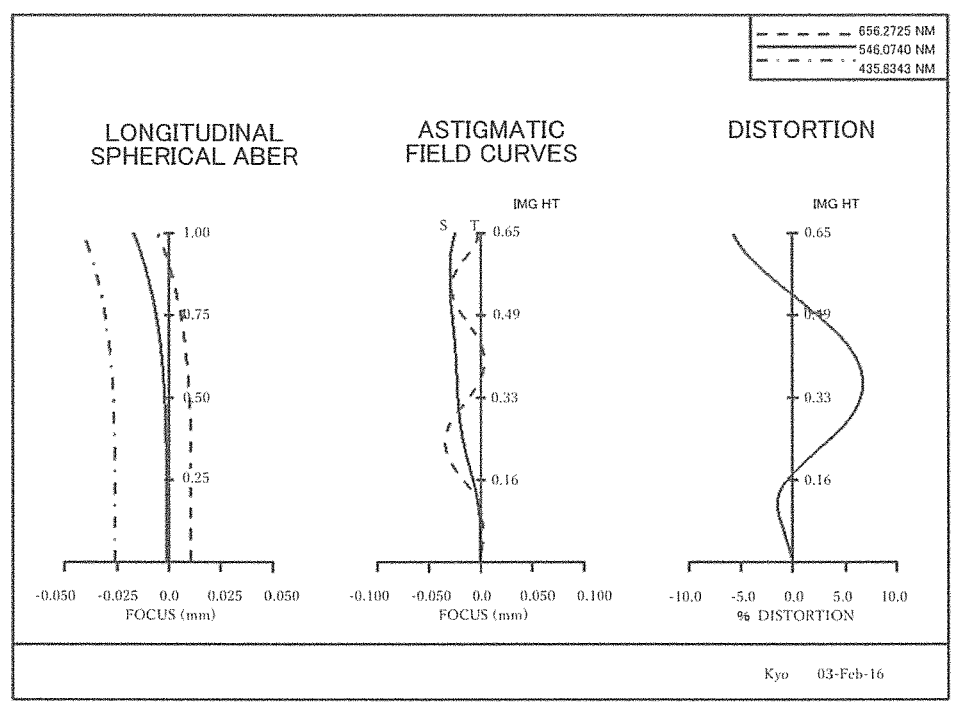
FIG. 31 is a graph illustrating aberration diagrams (spherical aberration, astigmatism, and field curvature) of a lens optical system of Example 2.
Figure 32:
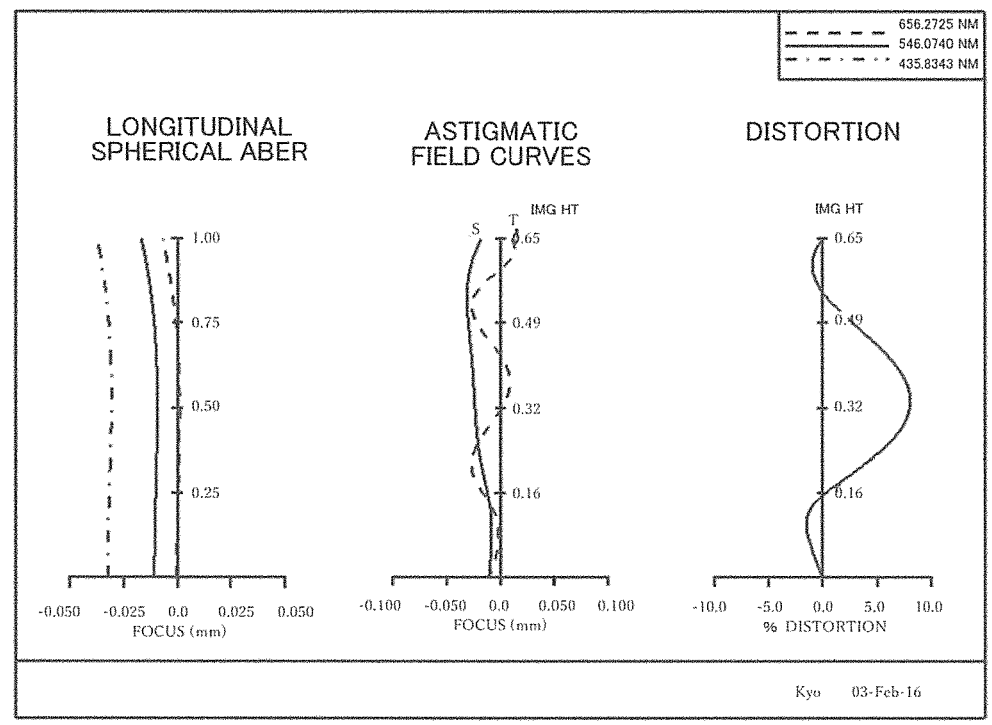
FIG. 32 is a graph illustrating aberration diagrams (spherical aberration, astigmatism, and field curvature) of a lens optical system of Example 3.
Figure 33:
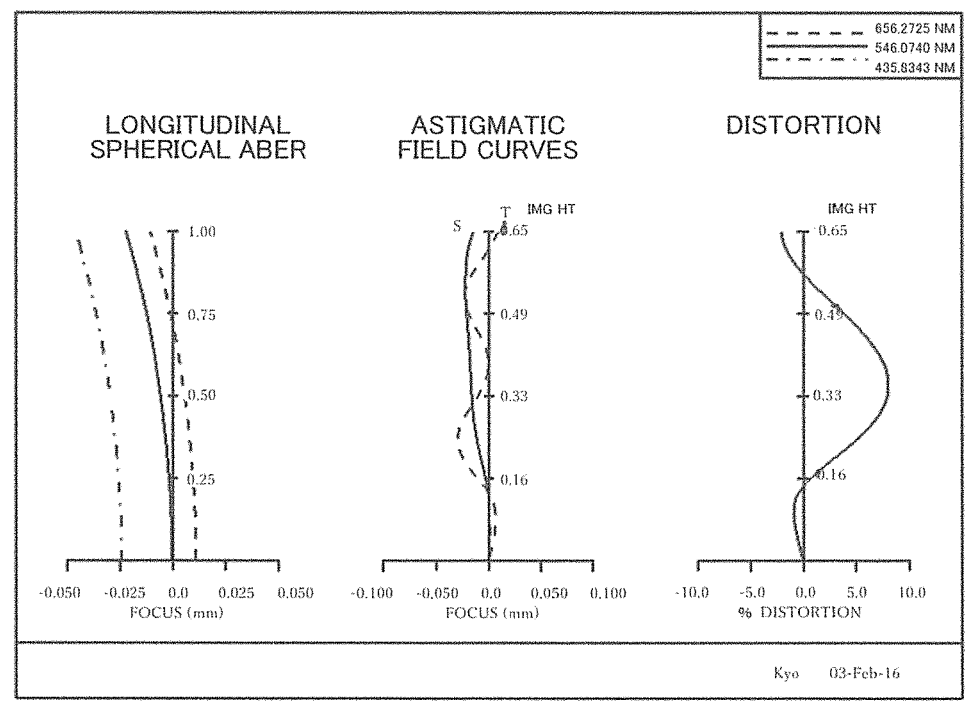
FIG. 33 is a graph illustrating aberration diagrams (spherical aberration, astigmatism, and field curvature) of a lens optical system of Example 4.
Figure 34:
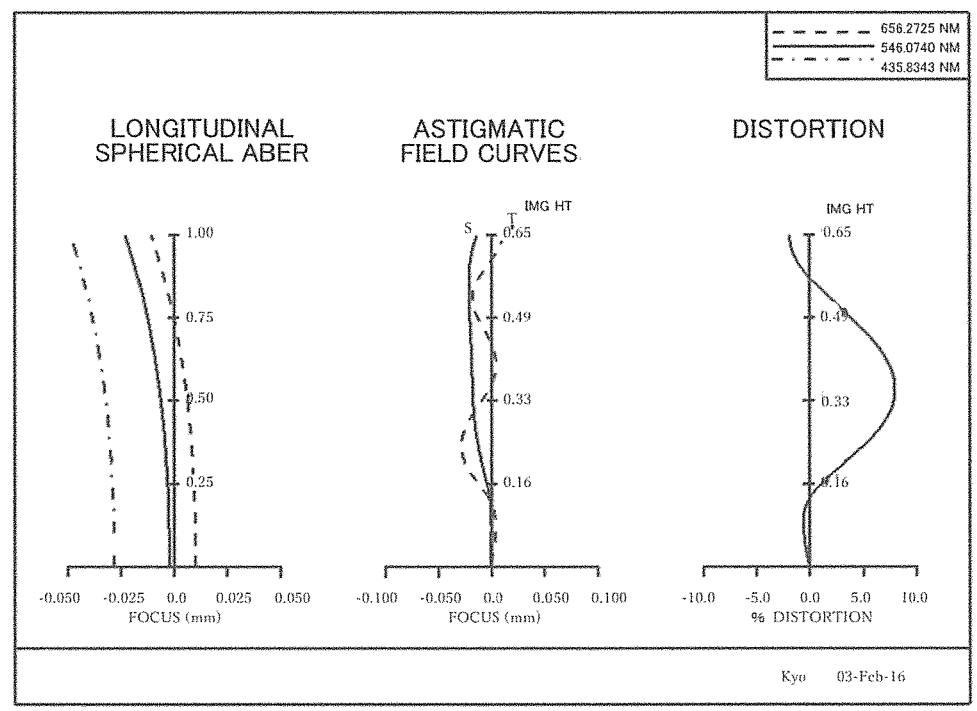
FIG. 34 is a graph illustrating aberration diagrams (spherical aberration, astigmatism, and field curvature) of a lens optical system of Example 5.
Figure 35:
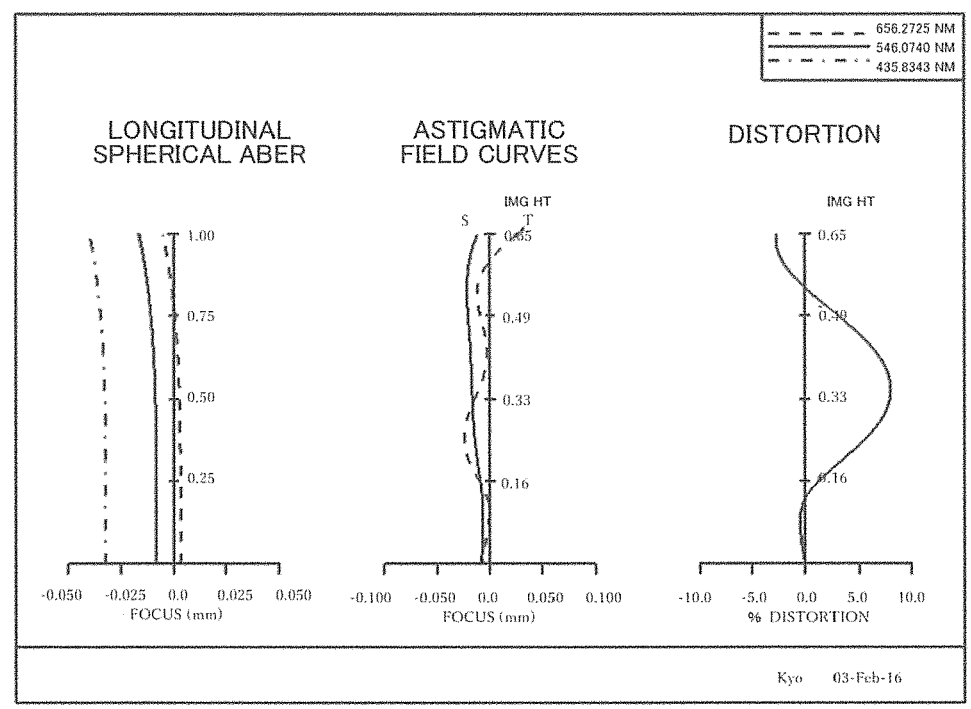
FIG. 35 is a graph illustrating aberration diagrams (spherical aberration, astigmatism, and field curvature) of a lens optical system of Example 6.
Figure 36:
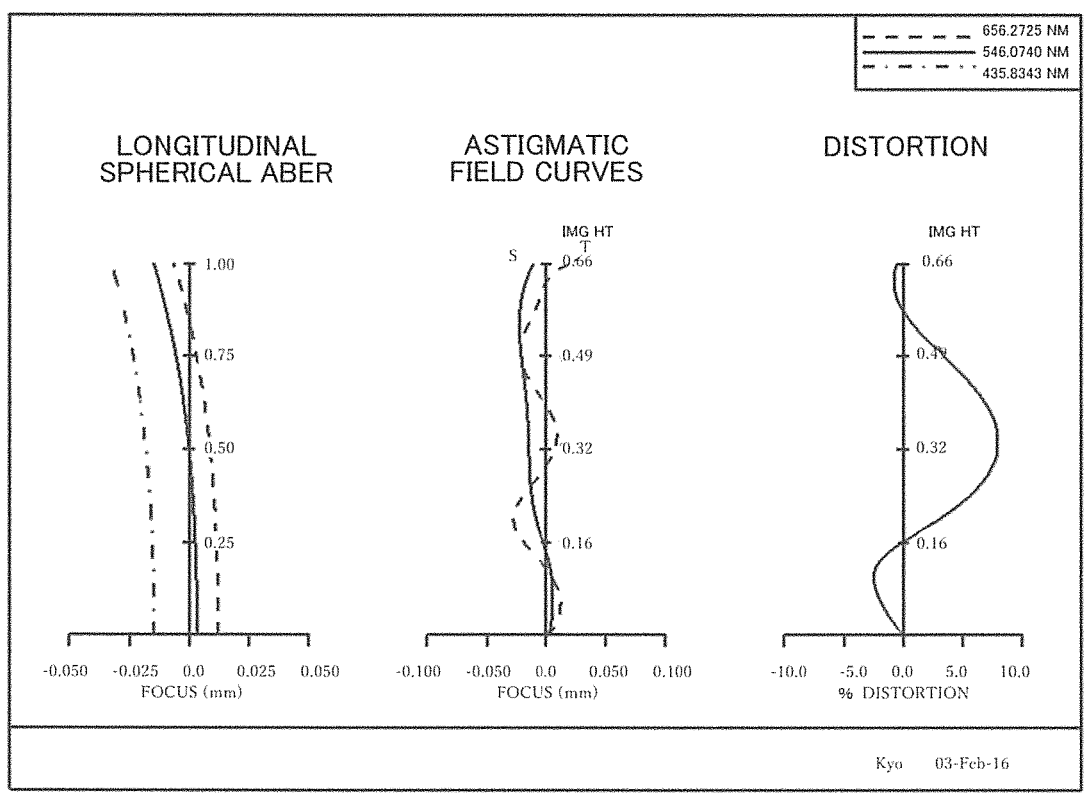
FIG. 36 is a graph illustrating aberration diagrams (spherical aberration, astigmatism, and field curvature) of a lens optical system of Example 7.

In the above embodiment, one camera 5 is provided for the pipe 2. Alternatively, a plurality of cameras 5 may be provided for the pipe 2. FIGS. 22A and 22B illustrate two cameras 5', 5' provided at symmetrical positions with respect to the pipe 2.

In this way, by simultaneously photographing images from different directions, information about the depth direction can also be obtained, and the operation can quickly and safely be performed.

Since the other configurations are the same as those in the above embodiment, the same reference numerals are denoted, and the description will be omitted.

Although the trocars of the embodiments of the present disclosure and the low height type lens optical system used in the trocar have been described above, the present disclosure is not limited to the above embodiments, but various improvements and changes can be made. For example, an illumination device may be provided in the camera 5 such that the operating field becomes brighter.

The low height type lens optical system can be used in applications other than the trocar. The trocar of the present disclosure can also suitably be used for an endoscopic surgical operation in the thoracic cavity.

EXAMPLES

A low height type lens optical system of the present disclosure will be described below with reference to Examples. The sections of the lens optical systems of Examples 1 to 7 are illustrated in FIGS. 23 to 29, respectively. In FIGS. 23 to 29, the left side of the drawing is the object side, the right side is the image side, and the stop S7 is also illustrated. The stop S7 in each drawing does not indicate the shape or the size, but indicates the position on the optical axis.

The surface number is denoted by Si (i=1 to 12) in the order from the object side surface S1 of the first lens L1, S0 is the object surface, S7 is the stop, S10 is the object side surface of a cover glass CG, S11 is the image side surface of the cover glass CG, and S12 is the imaging surface of the imaging sensor 16. Since the optical system of the present examples is based on the imaging in the abdominal cavity, the optical design is performed by setting the object to 50 mm in front of the object side face of the first lens L1.

The lens data of Example 1 is illustrated in Table 1, and the aspherical data is illustrated in Table 2. Table 1 illustrates a surface number of each surface Si of the imaging lens of the optical system, a curvature radius (unit: mm), a spacing, a lens material for each lens, and a refractive index with respect to a wavelength of 550 nm. A superscript * of the surface number indicates the aspheric surface.

TABLE 1

| Example 1 Surface data | | | | | |
|---|---|---|---|---|---|
| Surface number | | Curvature radius | Spacing | Material | Refractive index 550 nm |
| S0 | Object surface | inf | 50 | | |
| S1 | | inf | 0.8 | COC (Medical grade) | 1.5434 |
| S2 | | 3.598 | 0.3 | | |
| S3 | * | 3.842 | 0.4 | COC (Optical grade) | 1.5434 |
| S4 | * | 0.400 | 0.45 | | |
| S5 | * | 0.603 | 0.62 | | |
| S6 | * | 9.080 | 0.05 | PC (Optical grade) | 1.6355 |
| S7 | Stop | inf | 0.07 | | |
| S8 | * | 2.916 | 0.56 | COC (Optical grade) | 1.5434 |
| S9 | * | −0.380 | 0.11 | | |
| S10 | CG | inf | 0.4 | S-BSL7 (corresponding to BK7) | 1.5163 |
| S11 | CG | inf | 0.17 | | |
| S12 | Imaging surface | inf | | | |

The aspheric surface is represented by the following aspherical expression. In the aspheric expression, "Z" is a depth (mm) of the aspheric surface, "h" is a distance (mm) from the optical axis to the lens surface, "c" is a paraxial curvature (mm) (that is, c=1/R for a paraxial curvature radius R (mm)), "K" is a conic constant, and "Ai" is an aspherical coefficient. Table 2 illustrates "K" and "Ai" of each aspheric surface (see the mark * in Table 1) of Example. In Table 2, the numerical value "E-n" (n is an integer) indicates "×10$^{-n}$" and "E+n" indicates "×10$^{n}$".

$$Z = \frac{ch^2}{1 + \sqrt{1 - (1+K)c^2h^2}} + \sum A_i h^i$$

h: Distance from center of lens c = 1/R

TABLE 2

Example 1 Aspherical data

| Surface number | S3 | S4 | S5 | S6 | S8 | S9 |
|---|---|---|---|---|---|---|
| R | 3.8417E+00 | 4.0000E−01 | 6.0281E−01 | 9.0801E+00 | 2.9165E+00 | −3.8000E−01 |
| K | 1.5048E+01 | −8.0851E−01 | −5.0150E−01 | 5.0000E+01 | 1.0090E+01 | −1.9927E−01 |
| A4 | 1.4009E+00 | 8.0743E+00 | 1.8200E+00 | 4.6817E+00 | 2.3088E+00 | 1.3640E+00 |
| A6 | −4.6719E+00 | −7.8113E+01 | −2.6709E+01 | −3.3389E+01 | −6.0585E+00 | 5.7822E+01 |
| A8 | 5.5008E+00 | 2.4367E+02 | 1.4825E+02 | −3.1465E+03 | 1.4107E+03 | −4.7248E+02 |
| A10 | −2.3533E+00 | −2.6768E+02 | −2.6379E+02 | 1.1099E+05 | −1.9924E+04 | 2.1571E+03 |

Surface data and aspheric surface data of the lens optical systems of Examples 2 to 7 obtained in the same manner as in Example 1 are illustrated in Tables 3 to 14, respectively. The meanings of the symbols in the table are the same as those in Example 1.

TABLE 3

Example 2 Surface data

| Surface number | | Curvature radius | Spacing | Material | Refractive index 550 nm |
|---|---|---|---|---|---|
| S0 | Object surface | inf | 50.000 | | |
| S1 | | inf | 0.800 | COC (Medical grade) | 1.5434 |
| S2 | | 2.900 | 0.500 | | |
| S3 | * | 4.626 | 0.400 | COC (Optical grade) | 1.5434 |
| S4 | * | 0.418 | 0.371 | | |
| S5 | * | 0.526 | 0.603 | | |
| S6 | * | 3.649 | 0.050 | PC (Optical grade) | 1.6355 |
| S7 | Stop | inf | 0.070 | | |
| S8 | * | 3.831 | 0.602 | COC (Optical grade) | 1.5434 |
| S9 | * | −0.350 | 0.110 | | |
| S10 | CG | inf | 0.400 | S-BSL7 (corresponding to BK7) | 1.5163 |
| S11 | CG | inf | 0.148 | | |
| S12 | Imaging surface | inf | | | |

TABLE 4

Example 2 Aspherical data

| Surface number | S3 | S4 | S5 | S6 | S8 | S9 |
|---|---|---|---|---|---|---|
| R | 4.6257E+00 | 4.1796E−01 | 5.2622E−01 | 3.6494E+00 | 3.8306E+00 | −3.5000E−01 |
| K | 1.3974E+01 | −8.0376E−01 | −5.1974E−01 | −5.0000E+01 | 3.7094E+00 | −4.7379E−01 |
| A4 | 1.4512E+00 | 7.9960E+00 | 2.0374E+00 | 5.1828E+00 | −1.0700E+00 | 1.6350E−01 |
| A6 | −4.6479E+00 | −7.7623E+01 | −2.7902E+01 | −8.1709E+01 | 7.0690E+01 | 6.0214E+01 |
| A8 | 5.5230E+00 | 2.4394E+02 | 1.3574E+02 | −2.3768E+02 | 6.9938E+02 | −5.1149E+02 |
| A10 | −2.3207E+00 | −2.7168E+02 | −2.3867E+02 | 8.8041E+04 | −1.6088E+04 | 1.9255E+03 |

TABLE 5

Example 3 Surface data

| | Surface number | Curvature radius | Spacing | Material | Refractive index 550 nm |
|---|---|---|---|---|---|
| S0 | Object surface | inf | 50.000 | | |
| S1 | | inf | 0.800 | COC (Medical grade) | 1.5434 |
| S2 | | 10.611 | 0.400 | | |
| S3 | * | 4.470 | 0.400 | COC (Optical grade) | 1.5434 |
| S4 | * | 0.377 | 0.445 | | |
| S5 | * | 0.524 | 0.461 | | |
| S6 | * | 3.900 | 0.050 | PC (Optical grade) | 1.6355 |
| S7 | Stop | inf | 0.070 | | |
| S8 | * | 2.337 | 0.447 | COC (Optical grade) | 1.5434 |
| S9 | * | −0.352 | 0.110 | | |
| S10 | CG | inf | 0.400 | S-BSL7 (corresponding to BK7) | 1.5163 |
| S11 | CG | inf | 0.110 | | |
| S12 | Imaging surface | inf | | | |

TABLE 6

Example 3 Aspherical data

| Surface number | S3 | S4 | S5 | S6 | S8 | S9 |
|---|---|---|---|---|---|---|
| R | 4.4695E+00 | 3.7717E−01 | 5.2353E−01 | 3.9003E+00 | 2.3368E+00 | −3.5162E−01 |
| K | 2.0701E+01 | −8.4479E−01 | −6.0206E−01 | −1.8327E+01 | −2.6256E+01 | −7.0569E−01 |
| A4 | 1.3988E+00 | 9.4398E+00 | 1.4378E+00 | 8.5794E+00 | 1.6577E+00 | −1.8093E+00 |
| A6 | −4.5460E+00 | −9.1538E+01 | −1.6781E+01 | −3.2320E+02 | 5.6108E+01 | 1.5819E+02 |
| A8 | 5.2096E+00 | 2.7548E+02 | 5.0674E+01 | 1.3146E+04 | 1.0063E+03 | −1.9087E+03 |
| A10 | −2.1447E+00 | −2.5764E+02 | 3.2224E+02 | −1.5447E+05 | −1.9386E+04 | 9.6476E+03 |

TABLE 7

Example 4 Surface data

| | Surface number | Curvature radius | Spacing | Material | Refractive index 550 nm |
|---|---|---|---|---|---|
| S0 | Object surface | inf | 50.000 | | |
| S1 | | inf | 0.800 | COC (Medical grade) | 1.5434 |
| S2 | | 2.900 | 0.507 | | |
| S3 | * | 3.770 | 0.400 | COC (Optical grade) | 1.5434 |
| S4 | * | 0.400 | 0.420 | | |
| S5 | * | 0.463 | 0.527 | | |
| S6 | * | 1.317 | 0.050 | PC (Optical grade) | 1.6355 |

TABLE 7-continued

Example 4 Surface data

| Surface number | | Curvature radius | Spacing | Material | Refractive index 550 nm |
|---|---|---|---|---|---|
| S7 | Stop | inf | 0.070 | | |
| S8 | * | 2.473 | 0.519 | COC (Optical grade) | 1.5434 |
| S9 | * | −0.338 | 0.110 | | |
| S10 | CG | inf | 0.400 | S-BSL7 (corresponding to BK7) | 1.5163 |
| S11 | CG | inf | 0.130 | | |
| S12 | Imaging surface | inf | | | |

TABLE 8

Example 4 Aspherical data

| Surface number | S3 | S4 | S5 | S6 | S8 | S9 |
|---|---|---|---|---|---|---|
| R | 3.7701E+00 | 4.0002E−01 | 4.6307E−01 | 1.3172E+00 | 2.4727E+00 | −3.3792E−01 |
| K | 1.4407E+01 | −8.0592E−01 | −4.7440E−01 | 2.2041E+01 | −5.0000E+01 | −5.4878E−01 |
| A4 | 1.4839E+00 | 7.9298E+00 | 1.9382E+00 | 3.7811E+00 | 1.1711E+00 | 6.8188E−01 |
| A6 | −4.6681E+00 | −7.7604E+01 | −2.8015E+01 | 8.5000E+00 | 1.8177E+01 | 5.7403E+01 |
| A8 | 5.4962E+00 | 2.4454E+02 | 1.4352E+02 | −3.9555E+03 | 9.6781E+02 | −5.4085E+02 |
| A10 | −2.3446E+00 | −2.6949E+02 | −1.7748E+02 | 1.2699E+05 | −1.3455E+04 | 2.4039E+03 |

TABLE 9

Example 5 Surface data

| Surface number | | Curvature radius | Spacing | Material | Refractive index 550 nm |
|---|---|---|---|---|---|
| S0 | Object surface | inf | 50.000 | | |
| S1 | | inf | 0.800 | COC (Medical grade) | 1.5434 |
| S2 | | 2.936 | 0.050 | | |
| S3 | * | 3.295 | 0.400 | COC (Optical grade) | 1.5434 |
| S4 | * | 0.375 | 0.451 | | |
| S5 | * | 0.454 | 0.496 | | |
| S6 | * | 1.137 | 0.050 | PC (Optical grade) | 1.6355 |
| S7 | Stop | inf | 0.070 | | |
| S8 | * | 2.943 | 0.485 | COC (Optical grade) | 1.5434 |
| S9 | * | −0.351 | 0.110 | | |
| S10 | CG | inf | 0.400 | S-BSL7 (corresponding to BK7) | 1.5163 |
| S11 | CG | inf | 0.179 | | |
| S12 | Imaging surface | inf | | | |

TABLE 10

Example 5 Aspherical data

| Surface number | S3 | S4 | S5 | S6 | S8 | S9 |
|---|---|---|---|---|---|---|
| R | 3.2950E+00 | 3.7485E−01 | 4.5372E−01 | 1.1373E+00 | 2.9434E+00 | −3.5062E−01 |
| K | 1.0587E+01 | −8.5384E−01 | −4.1255E−01 | 3.9439E+01 | −5.0000E+01 | −7.4124E−01 |
| A4 | 1.4081E+00 | 7.6336E+00 | 1.6268E+00 | 2.8444E+00 | −2.5486E−02 | −7.1660E−01 |
| A6 | −4.6542E+00 | −7.7678E+01 | −2.3271E+01 | −1.3050E+02 | 6.9389E+01 | 6.2110E+01 |
| A8 | 5.4844E+00 | 2.4582E+02 | 1.0891E+02 | 2.0617E+03 | 2.0715E+01 | −6.7790E+02 |
| A10 | −2.3302E+00 | −2.7030E+02 | −3.8129E+01 | −6.6593E+04 | −5.5797E+03 | 3.1162E+03 |

TABLE 11

Example 6 Surface data

| Surface number | | Curvature radius | Spacing | Material | Refractive index 550 nm |
|---|---|---|---|---|---|
| S0 | Object surface | inf | 50.000 | | |
| S1 | | inf | 0.800 | COC (Medical grade) | 1.5434 |
| S2 | | 2.500 | 0.500 | | |
| S3 | * | 2.451 | 0.400 | COC (Optical grade) | 1.5434 |
| S4 | * | 0.300 | 0.331 | | |
| S5 | * | 0.421 | 0.530 | | |
| S6 | * | 1.874 | 0.050 | PC (Optical grade) | 1.6355 |
| S7 | Stop | inf | 0.070 | | |
| S8 | * | 1.503 | 0.473 | COC (Optical grade) | 1.5434 |
| S9 | * | −0.341 | 0.110 | | |
| S10 | CG | inf | 0.400 | S-BSL7 (corresponding to BK7) | 1.5163 |
| S11 | CG | inf | 0.100 | | |
| S12 | Imaging surface | inf | | | |

TABLE 12

Aspherical data
Example 6 Aspherical data

| Surface number | S3 | S4 | S5 | S6 | S8 | S9 |
|---|---|---|---|---|---|---|
| R | 2.4515E+00 | 3.0000E−01 | 4.2144E−01 | 1.8738E+00 | 1.5028E+00 | −3.4097E−01 |
| K | 5.4597E+00 | −9.0147E−01 | −3.7598E−01 | 5.0000E+01 | −1.4128E+01 | −8.9524E−01 |
| A4 | 1.3335E+00 | 7.9058E+00 | 4.7254E−01 | 4.3884E+00 | −1.0111E−01 | −6.4720E−01 |
| A6 | −4.3076E+00 | −8.7092E+01 | −1.0419E+01 | −8.4711E+01 | 8.5533E+01 | 8.6263E+01 |
| A8 | 5.1375E+00 | 2.7591E+02 | −2.1835E+01 | 6.0430E+02 | −7.2769E+02 | −9.2159E+02 |
| A10 | −2.1921E+00 | −2.5960E+02 | 2.6798E+02 | 3.5259E+04 | 2.2038E+03 | 4.1801E+03 |

TABLE 13

Example 7 Surface data

| Surface number | | Curvature radius | Spacing | Material | Refractive index 550 nm |
|---|---|---|---|---|---|
| S0 | Object surface | inf | 50.000 | | |
| S1 | | inf | 0.800 | COC (Medical grade) | 1.5434 |
| S2 | | 2.900 | 0.500 | | |
| S3 | * | 2.610 | 0.400 | COC (Optical grade) | 1.5434 |
| S4 | * | 0.438 | 0.445 | | |
| S5 | * | 0.586 | 0.613 | | |
| S6 | * | 2.708 | 0.050 | PC (Optical grade) | 1.6355 |
| S7 | Stop | inf | 0.070 | | |
| S8 | * | 2.775 | 0.498 | COC (Optical grade) | 1.5434 |
| S9 | * | −0.310 | 0.110 | | |
| S10 | CG | inf | 0.400 | S-BSL7 (corresponding to BK7) | 1.5163 |
| S11 | CG | inf | 0.100 | | |
| S12 | Imaging surface | inf | | | |

TABLE 14

Example 7 Aspherical data

| Surface number | S3 | S4 | S5 | S6 | S8 | S9 |
|---|---|---|---|---|---|---|
| R | 2.6103E+00 | 4.3803E−01 | 5.8605E−01 | 2.7081E+00 | 2.7752E+00 | −3.0963E−01 |
| K | 5.9060E+00 | −6.1380E−01 | −4.9807E−01 | −3.9077E+01 | 1.5071E+01 | −8.5695E−01 |
| A4 | 1.7449E+00 | 1.0341E+01 | 2.2755E+00 | 5.5394E+00 | −3.6267E−01 | −1.8872E+00 |
| A6 | −4.9782E+00 | −8.4807E+01 | −2.7337E+01 | −8.0827E+01 | 7.4807E+01 | 1.0173E+02 |
| A8 | 5.3139E+00 | 2.3990E+02 | 1.4019E+02 | −1.2694E+02 | −2.8209E+02 | −1.0458E+03 |
| A10 | −2.0877E+00 | −2.4785E+02 | −2.4528E+02 | 3.9794E+04 | −1.4729E+03 | 4.4562E+03 |

Table 15 illustrates the focal length f of the whole system, the focal lengths of the first to fourth lenses, and the values corresponding to the expressions (1) to (3) in the lens optical systems of Examples 1 to 7. All Examples 1 to 7 satisfy the conditional expressions (1) to (3).

In Table 15, mm is used as the unit of the numerical value for the length by way of example. Since the optical system can be used even in proportional expansion or proportional reduction, another suitable unit can also be used.

TABLE 15

| | Example 1 | Example 2 | Example 3 | Example 4 | Example 5 | Example 6 | Example 7 |
|---|---|---|---|---|---|---|---|
| Focal length f | 0.408 | 0.409 | 0.390 | 0.390 | 0.420 | 0.358 | 0.361 |
| Maximam aperture | 3.2 | 3.2 | 3.2 | 3.2 | 3.2 | 3.2 | 3.2 |
| Angle of view (2ω) | 120 | 119 | 118 | 119 | 115 | 124 | 123 |
| Focal length of L1 $f_1$ | −6.577 | −5.302 | −19.398 | −5.302 | −5.367 | −4.570 | −5.302 |
| Focal length of L2 f2 | −0.851 | −0.869 | −0.780 | −0.854 | −0.813 | −0.669 | −1.029 |
| Focal length of L3 f3 | 0.979 | 0.892 | 0.896 | 0.898 | 0.917 | 0.742 | 1.048 |
| Focal length of L4 f4 | 0.654 | 0.618 | 0.594 | 0.581 | 0.604 | 0.559 | 0.540 |
| Composite focal length of L2 to L3 $f_{234}$ | 0.468 | 0.500 | 0.410 | 0.476 | 0.473 | 0.444 | 0.448 |
| Spacing between L1 and L2 t2 | 0.300 | 0.500 | 0.400 | 0.507 | 0.050 | 0.500 | 0.500 |
| Expression (1) | 0.872 | 0.818 | 0.951 | 0.820 | 0.888 | 0.806 | 0.807 |
| Expression (2) | 0.735 | 1.222 | 1.026 | 1.300 | 0.119 | 1.398 | 1.384 |
| Expression (3) | 1.819 | 1.738 | 1.903 | 1.796 | 1.718 | 1.508 | 2.300 |

Aberration diagrams of the lens optical systems of Examples 1 to 7 are illustrated in FIGS. 30 to 36, respectively. FIGS. 30 to 36 each illustrate spherical aberration, astigmatism, and field curvature (distortion) in the lens optical system.

In the graph of the spherical aberration, a broken line indicates the wavelength of 656.3 nm, a solid line indicates the wavelength of 546.1 nm, and an alternate long and short dash line indicates the wavelength of 436.8 nm.

In the graph of the astigmatism, the broken line means tangential and the solid line means sagittal.

From Examples, when the low height type lens optical system of the present disclosure is used, a wide-angle visual field exceeding the view angle of 110 degrees can be secured, and the assembling tolerance can be relaxed using the spherical surface as the first lens, and a stable optical system can be provided.

What is claimed is:

1. A trocar for inserting a surgical instrument in a body, comprising:
    a pipe comprising an inner cylinder and an outer cylinder configured to slide in an axial direction relative to the inner cylinder;
    a head located on a proximal end of the pipe,
    a camera that is journaled at a distal end notch of the inner cylinder and configured to rotate between a deployment state in which the camera rotates to the outside of the pipe and a storage state in which the camera is stored inside the pipe; and
    a deployment and storage mechanism comprising an elastic member in the inner cylinder that biases the camera to the deployment state, and the outer cylinder being configured to store the camera in the pipe against biasing force of the elastic member while sliding toward a distal end of the pipe,
    wherein
    the camera comprises a camera housing and an imaging unit housing attached to a front surface of the camera housing, a lens and an imaging sensor being attached to the imaging unit housing, and
    the camera housing comprises a rear surface that is flush with the inner cylinder in the storage state.

2. The trocar according to claim 1, wherein the camera comprises a camera holding mechanism in which both ends of the camera in a width direction orthogonal to the pipe are journaled in the inner cylinder, and one end of the elastic member is connected to a position outwardly in a radial direction from a journaling point of the camera so as to bias the camera toward a rear side of the pipe.

3. The trocar according to claim 1, comprising a lock configured to lock the camera in the storage state in the pipe.

4. The trocar according to claim 1, wherein the outer cylinder is shorter than the inner cylinder so as to be located behind the camera in a state in which the camera is deployed to the outside of the pipe from the distal end notch of the inner cylinder.

5. The trocar according to claim 1, wherein a tubular sealing member is interposed between the outer cylinder and the inner cylinder.

6. The trocar according to claim 1, wherein a controller configured to control the imaging sensor is provided inside a connector provided on an outer surface of the head.

7. The trocar according to claim 6, wherein a cable is inserted between the outer cylinder and the inner cylinder; and one end of the cable is connected to the imaging sensor, and the other end is connected to the controller.

8. The trocar according to claim 7, wherein an external cable configured to transmit an image signal is connected to the controller.

9. The trocar according to claim 6, wherein the connector is disposed at a position different from a mounting position of the camera in a circumferential direction of the head.

10. The trocar according to claim 9, wherein the connector is disposed at a position symmetrical to an attachment position of the camera with respect to an axial center of the pipe in a circumferential direction of the head.

11. The trocar according to claim 1, wherein
the camera comprises a first optical element, a second optical element, and an imaging sensor,
the first optical element is a translucent protective cover as a first lens disposed on a front surface of the second optical element,
the second optical element includes a second lens, a third lens, and a fourth lens,
the first lens having negative power, the second lens having negative power, the third lens having positive power, and the fourth lens having positive power are disposed in order from an object side,
the first lens is a plano-concave lens in which a concave surface is formed on an image surface side,
the second lens is a meniscus concave lens in which a convex surface is formed on the object side,
the third lens is a meniscus convex lens in which a convex surface is formed on the object side,
the fourth lens is a biconvex lens,
a stop is provided between the third lens and the fourth lens, and ail both sides in the second to fourth lenses are constructed with an aspherical surface.

12. The trocar according to claim 11, wherein the first lens is a plano-concave lens having a flat surface on the object side and a spherical surface on the image side.

13. The trocar according to claim 12, wherein
all the lenses from the first lens to the fourth lens are resin lenses.

14. The trocar according to claim 12, wherein assuming that f is a focal length of the first lens, and that $f_{234}$ is a composite focal length of the second lens, the third lens, and the fourth lens, the following conditional expression is satisfied:

$$0.80 < f/f_{234} < 0.96 \quad \text{(Expression 1)}$$

15. The trocar according to claim 12, wherein assuming that f is a focal length of the first lens, and that $t_2$ is a spacing on an optical axis between the first lens and the second lens, the following conditional expression is satisfied:

$$0.11 < \frac{t_2}{f} < 1.40. \quad \text{(Expression 2)}$$

16. The trocar according to claim 12, wherein assuming that $f_2$ is the focal length of the second lens, and that $f_{234}$ is the composite focal length of the second lens, the third lens, and the fourth lens, the following conditional expression is satisfied:

$$1.50 < \frac{|f_2|}{f_{234}} < 2.30. \quad \text{(Expression 3)}$$

17. A trocar for inserting a surgical instrument in a body, comprising:
a pipe comprising an inner cylinder and an outer cylinder configured to slide in an axial direction relative to the inner cylinder;
a camera that is journaled at a distal end of the inner cylinder and configured to rotate between a deployment state in which the camera rotates to the outside of the pipe and a storage state in which the camera is stored inside the pipe; and
a deployment and storage mechanism comprising an elastic member in the inner cylinder that biases the camera to the deployment state, and the outer cylinder being configured to store the camera in the pipe against biasing force of the elastic member while sliding toward a distal end of the pipe,
wherein
the camera comprises a camera housing and an imaging unit housing attached to a front surface of the camera housing, a lens and an imaging sensor being attached to the imaging unit housing, and
the camera housing comprises a rear surface that is flush with the inner cylinder in the storage state.

18. The trocar according to claim 17, wherein the camera comprises a camera holding mechanism in which both ends of the camera in a width direction orthogonal to the pipe are journaled in the inner cylinder, and one end of the elastic member is connected to a position outwardly in a radial direction from a journaling point of the camera so as to bias the camera toward a rear side of the pipe.

19. The trocar according to claim 17, wherein the outer cylinder is shorter than the inner cylinder so as to be located behind the camera in a state in which the camera is deployed to the outside of the pipe from the distal end notch of the inner cylinder.

20. The trocar according to claim 17, wherein a tubular sealing member is interposed between the outer cylinder and the inner cylinder.

* * * * *